United States Patent
Yan et al.

(10) Patent No.: US 6,653,116 B2
(45) Date of Patent: Nov. 25, 2003

(54) ISOLATED HUMAN KINASE PROTEINS

(75) Inventors: Chunhua Yan, Boyds, MD (US);
Ming-Hui Wei, Germantown, MD (US); Karen Ketchum, Germantown, MD (US); Gennady Merkulov, Baltimore, MD (US); Ellen M Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/153,921

(22) Filed: May 24, 2002

(65) Prior Publication Data

US 2002/0142430 A1 Oct. 3, 2002

Related U.S. Application Data

(62) Division of application No. 09/734,030, filed on Dec. 12, 2000, now Pat. No. 6,461,846.
(60) Provisional application No. 60/207,281, filed on May 30, 2000.

(51) Int. Cl.[7] ............................. C12N 9/12; C12N 1/20; C12N 15/00; C07K 1/00; C12Q 1/68
(52) U.S. Cl. ..................... 435/194; 435/320.1; 435/325; 435/252.3; 435/6; 530/350
(58) Field of Search ................................. 435/194, 325, 435/320.1, 6, 252.3; 530/350

(56) References Cited

FOREIGN PATENT DOCUMENTS

| EP | 1 130 094 A | 9/2001 |
|---|---|---|
| WO | WO 00 55177 A | 9/2000 |
| WO | WO 01 20004 A | 3/2001 |
| WO | WO 01 53312 A | 7/2001 |
| WO | WO 01 64905 A | 9/2001 |
| WO | WO 01 81555 A | 11/2001 |

OTHER PUBLICATIONS

PIR–73 Database, Accession No. 156542, Jul. 26, 1996, cited as Godbout et al. in the IDS.*
Cottage et al. "Three Receptor Genes for Plasminogen Related Growth Factors in the Genome of the Puffer Fish Fugu Rubripes." FEBS Letters, Elsevier Science Publishers, Amsterdam, NL, vol. 443, No. 3, pp. 370–374. Jan. 29, 1999. XP004259178.
Cottage A. J. "Calmodulin Binding Protein Kinase." Database SWISS PROT Online! May 1, 1999. XP002196600.
Godbout Martin et al. "1G5: A Calmodulin–binding, Vesicle–Associated, Protein Kinase–like Protein Enriched in Forebrain Neurites." Journal of Neuroscience, vol. 14, No. 1, 1994, pp. 1–13. XP001068816.
International Search report dated May 7, 2002.

* cited by examiner

Primary Examiner—Maryam Monshipouri
(74) Attorney, Agent, or Firm—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

4 Claims, 24 Drawing Sheets

```
   1 TCCGCCCCCG GCCCGGGGTG CGAATCCGGT GCCGGCAAGC GGCTGGCGAT
  51 GCTGGAGGTT CGCTAGCCGA AGCGGCTGCA TCTGGCGCCG CGTCTGCCCC
 101 GCGTGCTCGG AGCGGATTCT GCCCGCCGTC CCCGGAGCCC TCGGCGCCCC
 151 GCTGAGCCCG CGATCACTTC CTCCCTGTGA CCAACCGGCG CTGCAGGTTA
 201 GAGCCTGGCA ATGCCGTTTG GGTGTGTGAC TCTGGGCGAC AAGAAGAACT
 251 ATAACCAGCC ATCGGAGGTG ACTGACAGAT ATGATTTGGG ACAGGTCATC
 301 AAGACTGAGG AGTTTTGTGA AATCTTCCGG GCCAAGGACA AGACGACAGG
 351 CAAGCTGCAC ACCTGCAAGA AGTTCCAGAA GCGGGACGGC CGCAAGGTGC
 401 GGAAAGCTGC CAAGAACGAG ATAGGCATCC TCAAGATGGT GAAGCATCCC
 451 AACATCCTAC AGCTGGTGGA TGTGTTTGTG ACCCGCAAGG AGTACTTTAT
 501 CTTCCTGGAG CTGGCCACGG GGAGGGAGGT GTTTGACTGG ATCCTGGACC
 551 AGGGCTACTA CTCGGAGCGA GACACAAGCA ACGTGGTACG GCAAGTCCTG
 601 GAGGCCGTGG CCTATTTGCA CTCACTCAAG ATCGTGCACA GGAATCTCAA
 651 GCTGGAGAAC CTGGTTTACT ACAACCGGCT GAAGAACTCG AAGATTGTCA
 701 TCAGTGACTT CCATCTGGCT AAGCTAGAAA ATGGCCTCAT CAAGGAGCCC
 751 TGTGGGACCC CCGAGTATCT GGCCCCAGAG GTGGTAGGCC GGCAGCGGTA
 801 TGGACGCCCT GTGGACTGCT GGGCCATTGG AGTCATCATG TACATCCTGC
 851 TTTCAGGCAA TCCACCTTTC TATGAGGAGG TGGAAGAAGA TGATTATGAG
 901 AACCATGATA AGAATCTCTT CCGCAAGATC CTGGCTGGTG ACTATGAGTT
 951 TGACTCTCCA TATTGGGATG ATATTTCGCA GGCAGCCAAA GACCTGGTCA
1001 CAAGGCTGAT GGAGGTGGAG CAAGACCAGC GGATCACTGC AGAAGAGGCC
1051 ATCTCCCATG AGTGGATTTC TGGCAATGCT GCTTCTGATA AGAACATCAA
1101 GGATGGTGTC TGTGCCCAGA TTGAAAAGAA CTTTGCCAGG GCCAAGTGGA
1151 AGAAGGCTGT CCGAGTGACC ACCCTCATGA AACGGCTCCG GGCACCAGAG
1201 CAGTCCAGCA CGGCTGCAGC CCAGTCGGCC TCAGCCACAG ACACTGCCAC
1251 CCCCGGGGCT GCAGGTGGGG CCACAGCTGC AGCTGCGAGT GGAGCTACCT
1301 CAGCCCCTGA GGGTGATGCT GCTCGTGCTG CAAAGAGTGA TAATGTGGCC
1351 CCCGCAGACC GTAGTGCCAC CCCAGCCACA GATGGAAGTG CCACCCCAGC
1401 CACTGATGGC AGTGTCACCC CAGCCACCGA TGGAAGCATC ACTCCAGCCA
1451 CTGATGGGAG TGTCACCCCA GTCACTGACA GGAGCGCTAC TCCAGCCACT
1501 GATGGGAGAG CCACACCAGC CACAGAAGAG AGCACTGTGC CACCACCCA
1551 AAGCAGTGCC ATGCTGGCCA CCAAGGCAGC TGCCACCCCT GAGCCGGCTA
1601 TGGCCCAGCC GGACAGCACA GCCCCAGAGG GCGCCACAGG CCAGGCTCCA
1651 CCCTCTAGTA AAGGGGAAGA GGCTGCTGGT TATGCCCAGG AGTCTCAAAG
1701 GGAGGAGGCC AGCTGAGTAG GCAGCCTGGT GAGGGGGGGC AGGGGATGGG
1751 CAGGAGGGTG GGAGAGTGGA TGAGGGGCTT CTCACTGTAC ATAGAGTCAC
1801 TGGCATGATG CCCTCGCTCC CCATGCCCC CACATCCCAG TGGGGCATAA
1851 CTAGGGGTCA CGGGAGAGCA GTCTCGTCTC CTGTGTGTAT GTGTGTGAGT
1901 GGTGGGCAGG CCAGTGGCAG GGCCGGCCCC AGCCCCTGCA TGGATTCCTT
1951 GTGGCTTTTC TGTCTTTTGC TAGCTTCACC AGTTTCTGTT CCTTGTGGGA
2001 TGCTGCTCTA GGGATACTCA GGGGGCTCCT GCTCTCCTTC CCCTTCCCTT
2051 CTTGCCTCAC CATTCCCCTA GGCAGGCCCT GCAGGTCCCA CACTCTCCCA
2101 GGCCCTAAAC TTGGGCGGCC TTGCCCTGAG AGCTGGTCCT CCAGCGAGGC
2151 CCTGTCAGCG GTCTTAGGCT CCTGCACATG AAGGTGTGTG CCTGTGGTGT
2201 GTGGGCTGCT CTAGGAGCAG ATACAGGCTG GTATAGAGGA TGCAGAAAGG
2251 TAGGGCAGTA TGTTTAAGTC CAGACTTGGC ACATGGCTAG GGATACTGCT
2301 CACTAGCTGT GGAGGTCCTC AGGAGTGGAG AGAATGAGTA GGAGGGCAGA
2351 AGCTTCCATT TTTGTCCTTC CTAAGACCCT GTTATTTGTG TTATTTCCTG
2401 CCTTTCCGAG TCCTGCAGTG GGCTGCCCTG TACCCTGAAC CTCATGAGCC
2451 TCTAAGGGAA AGGAGGAACA ATTAGGACGT GGCAATGAGA CCTGGCAGGG
2501 CAGAGTACAA GCCCAGCACC CAGTGTCCCA GCCTTACTGG GTCCTTACCC
2551 TGGGCCAAAC AGGGAGGGCT GATACCTCCT TGCTCTTCCT AGATGCCCAC
2601 CTCCTACAAT CTCAGCCCAC AAGTCCTCTC CACCCTAGGG GGCTTGCTGC
2651 ATGGCAATAA CTCATAATCT GATTTGGAGG TTTGCCCTTT ACAGGGGCAG
2701 ATTTTCTGCT CAGTTCAACA ATGAAATGAA GAGGAACTCC CTCTTTCTAC
2751 AGCTCACTTC TATCAGAGGC CCAGGTGCCT CAGAGCCACA TTGAGTTGCT
2801 TTTTCTGGGA TGAGGAAGTA GGGTTAAACT CCCCAGTTTC CTGAGGGAGG
2851 CTCCTGACAG GTGCCCTTTG TCAGACCCTA CCACAGCCTG GATAGGCAGC
2901 CACATTGGTC CTCGCCCTTG CTCGGCACTC CGTGGTGGTC CTGCCCTTCT
```

FIGURE 1A

```
2951 CCCTGCATGC CTGTGGGTCT GCTCTGGTGT GTGAAGGTCG GTGGGTTAAC
3001 TGTGTGCCTA CTGAACCTGG CAAATAAACA TCACCCTGCA AAGCCAAAAA
3051 AAAAAAAAAA AAAAAAAAAA AAAAAAAAAA AAAAAAAAAA AAAAAAAAAA
3101 AAAAAAAAAA AAAAAAAAAA AAAA
```

FEATURES:
5'UTR:         1 - 210
Start Codon:   211
Stop Codon:    1714
3'UTR:         1717

Homologous proteins:
Top 10 BLAST Hits

|  | Score | E |
|---|---|---|
| gi\|2143639\|pir\|\|I56542 calmodulin-binding protein - rat >gi\|349... | 929 | 0.0 |
| gi\|7521914\|pir\|\|T30814 calmodulin-binding protein kinase - Fugu... | 598 | e-170 |
| gi\|3122310\|sp\|Q63450\|KCC1_RAT CALCIUM/CALMODULIN-DEPENDENT PROT... | 310 | 4e-83 |
| gi\|4502553\|ref\|NP_003647.1\| calcium/calmodulin-dependent protei... | 309 | 9e-83 |
| gi\|3114436\|pdb\|1A06\|   Calmodulin-Dependent Protein Kinase Fro... | 303 | 7e-81 |
| gi\|406113\|gb\|AAA19670.1\| (L24907) protein kinase I [Rattus norv... | 299 | 1e-79 |
| gi\|9966875\|ref\|NP_065130.1\| CamKI-like protein kinase [Homo sap... | 299 | 1e-79 |
| gi\|3893099\|emb\|CAA76937.1\| (Y17917) calcium/calmodulin dependen... | 288 | 3e-76 |
| gi\|4007153\|emb\|CAA19296.1\| (AL023754) dJ272L16.1 (Rat Ca2+/Calm... | 286 | 1e-75 |
| gi\|4678722\|emb\|CAB41259.1\| (AL049688) hypothetical protein [Hom... | 286 | 1e-75 |

BLAST to dbEST:

|  | Score | E |
|---|---|---|
| gi\|11264319 /dataset=dbest /taxon=96... | 1057 | 0.0 |
| gi\|11126214 /dataset=dbest /taxon=96... | 989 | 0.0 |
| gi\|11259094 /dataset=dbest /taxon=96... | 963 | 0.0 |
| gi\|11260705 /dataset=dbest /taxon=96... | 896 | 0.0 |
| gi\|708663 /dataset=dbest /taxon=9606 /... | 611 | e-172 |
| gi\|10215012 /dataset=dbest /taxon=96... | 601 | e-169 |
| gi\|11099650 /dataset=dbest /taxon=960... | 577 | e-162 |
| gi\|831534 /dataset=dbest /taxon=9606 /... | 535 | e-150 |
| gi\|9136656 /dataset=dbest /taxon=9606... | 529 | e-148 |
| gi\|2001736 /dataset=dbest /taxon=9606 ... | 509 | e-142 |

EXPRESSION INFORMATION FOR MODULATORY USE:
library source:
Expression information from BLAST dbEST hits:
gi\|11264319  Brain
gi\|11126214  Lung
gi\|11259094  Brain
gi\|11260705  Brain
gi\|708663    Infant brain
gi\|10215012  Lung
gi\|11099650  Brain
gi\|831534    Infant brain
gi\|9136656   Brain
gi\|2001736   Infant brain Expression information from PCR-based tissue screening panels:
Infant brain, hippocampus

FIGURE 1B

```
  1 MPFGCVTLGD KKNYNQPSEV TDRYDLGQVI KTEEFCEIFR AKDKTTGKLH
 51 TCKKFQKRDG RKVRKAAKNE IGILKMVKHP NILQLVDVFV TRKEYFIFLE
101 LATGREVFDW ILDQGYYSER DTSNVVRQVL EAVAYLHSLK IVHRNLKLEN
151 LVYYNRLKNS KIVISDFHLA KLENGLIKEP CGTPEYLAPE VVGRQRYGRP
201 VDCWAIGVIM YILLSGNPPF YEEVEEDDYE NHDKNLFRKI LAGDYEFDSP
251 YWDDISQAAK DLVTRLMEVE QDQRITAEEA ISHEWISGNA ASDKNIKDGV
301 CAQIEKNFAR AKWKKAVRVT TLMKRLRAPE QSSTAAAQSA SATDTATPGA
351 AGGATAAAAS GATSAPEGDA ARAAKSDNVA PADRSATPAT DGSATPATDG
401 SVTPATDGSI TPATDGSVTP VTDRSATPAT DGRATPATEE STVPTTQSSA
451 MLATKAAATP EPAMAQPDST APEGATGQAP PSSKGEEAAG YAQESQREEA
501 S
```

FEATURES:
Functional domains and key regions:
[1] PDOC00005 PS00005 PKC_PHOSPHO_SITE
Protein kinase C phosphorylation site

```
Number of matches: 11
         1      21-23 TDR
         2    422-424 TDR
         3      46-48 TGK
         4      51-53 TCK
         5      91-93 TRK
         6    103-105 TGR
         7    118-120 SER
         8    138-140 SLK
         9    292-294 SDK
        10      21-23 TDR
        11    422-424 TDR
```

[2] PDOC00006 PS00006 CK2_PHOSPHO_SITE
Casein kinase II phosphorylation site

```
Number of matches: 10
         1      7-10 TLGD
         2     91-94 TRKE
         3   103-106 TGRE
         4   118-121 SERD
         5   276-279 TAEE
         6   341-344 SATD
         7   364-367 SAPE
         8   470-473 TAPE
         9   483-486 SKGE
        10   495-498 SQRE
```

[3] PDOC00007 PS00007 TYR_PHOSPHO_SITE
Tyrosine kinase phosphorylation site

```
Number of matches: 2
         1   127-135 RQVLEAVAY
         2   484-491 KGEEAAGY
```

FIGURE 2A

[4] PDOC00008 PS00008 MYRISTYL
N-myristoylation site

Number of matches: 4
1    288-293    GNAASD
2    349-354    GAAGGA
3    352-357    GGATAA
4    353-358    GATAAA

[5] PDOC00009 PS00009 AMIDATION
Amidation site 59-62    DGRK

Membrane spanning structure and domains:
 Helix  Begin  End   Score  Certainty
   1     207   227   1.342  Certain
   2     351   371   1.250  Certain BLAST Alignment to Top Hit:
>gi|2143639|pir||I56542 calmodulin-binding protein - rat
 gb|AAA16633.1| (L22557) calmodulin-binding protein [Rattus norvegicus]
         Length = 504

Score = 929 bits (2375), Expect = 0.0
Identities = 468/509 (91%), Positives = 473/509 (91%), Gaps = 8/509 (1%)
Frame = +1

Query:  211  MPFGCVTLGDKKNYNQPSEVTDRYDLGQVIKTEEFCEIFRAKDKTTGKLHTCKKFQKRDG  390
             MPFGCVTLGDKKNYNQPSEVTDRYDLGQV+KTEEFCEIFRAKDKTTGKLHTCKKFQKRDG
Sbjct:   1   MPFGCVTLGDKKNYNQPSEVTDRYDLGQVVKTEEFCEIFRAKDKTTGKLHTCKKFQKRDG   60

Query:  391  RKVRKAAKNEIGILKMVKHPNILQLVDVFVTRKEYFIFLELATGREVFDWILDQGYYSER  570
             RKVRKAAKNEIGILKMVKHPNILQLVDVFVTRKEYFIFLELATGREVFDWILDQGYYSER
Sbjct:   61  RKVRKAAKNEIGILKMVKHPNILQLVDVFVTRKEYFIFLELATGREVFDWILDQGYYSER  120

Query:  571  DTSNVVRQVLEAVAYLHSLKIVHRNLKLENLVYYNRLKNSKIVISDFHLAKLENGLIKEP  750
             DTSNVVRQVLEAVAYLHSLKIVHRNLKLENLVYYNRLKNSKIVISDFHLAKLENGLIKEP
Sbjct:  121  DTSNVVRQVLEAVAYLHSLKIVHRNLKLENLVYYNRLKNSKIVISDFHLAKLENGLIKEP  180

Query:  751  CGTPEYLAPEVVGRQRYGRPVDCWAIGVIMYILLSGNPPFYEEVEEDDYENHDKNLFRKI  930
             CGTPEYLAPEVVGRQRYGRPVDCWAIGVIMYILLSGNPPFYEEVEEDDYENHDKNLFRKI
Sbjct:  181  CGTPEYLAPEVVGRQRYGRPVDCWAIGVIMYILLSGNPPFYEEVEEDDYENHDKNLFRKI  240

Query:  931  LAGDYEFDSPYWDDISQAAKDLVTRLMEVEQDQRITAEEAISHEWISGNAASDKNIKDGV  1110
             LAGDYEFDSPYWDDISQAAKDLVTRLMEVEQDQRITAEEAISHEWISGNAASDKNIKDGV
Sbjct:  241  LAGDYEFDSPYWDDISQAAKDLVTRLMEVEQDQRITAEEAISHEWISGNAASDKNIKDGV  300

Query:  1111 CAQIEKNFARAKWKKAVRVTTLMKRLRAPEQSSTAAAQSASATDTATPGAAGGATAAAAS  1290
             CAQIEKNFARAKWKKAVRVTTLMKRLRAPEQS TAA      +D ATPGAAGGA AAAA
Sbjct:  301  CAQIEKNFARAKWKKAVRVTTLMKRLRAPEQSGTAA-----TSDAATPGAAGGAVAAAAG  355

Query:  1291 G--------ATSAPEGDAARAAKSDNVAPADRSATPATDGSATPATDGSVTPATDGSITP  1446
             G        AT   GDA  AAKSD++A ADRSATPATDGSATPATDGSVTPATDGSITP
Sbjct:  356  GAAPASGASATVGTGGDAGCAAKSDDMASADRSATPATDGSATPATDGSVTPATDGSITP  415

FIGURE 2B

```
Query: 1447  ATDGSVTPVTDRSATPATDGRATPATEESTVPTTQSSAMLATKAAATPEPAMAQPDSTAP 1626
             ATDGSVTP TDRSATPATDGRATPATEESTVP  QSSA  A KAAATPEPA+AQPDSTA
Sbjct:  416  ATDGSVTPATDRSATPATDGRATPATEESTVPAAQSSAAPAAKAAATPEPAVAQPDSTAL 475

Query: 1627  EGATGQAPPSSKGEEAAGYAQESQREEAS 1713
             EGATGQAPPSSKGEEA G AQESQR E S
Sbjct:  476  EGATGQAPPSSKGEEATGCAQESQRVETS 504

Score = 34.4 bits (77), Expect = 7.1
 Identities = 42/158 (26%), Positives = 60/158 (37%), Gaps = 5/158 (3%)
 Frame = -3

Query: 1673  ASSPLLEGGAWPVAPSGAVLSGWATA--GSGVAAALVASMALLWVVGTVLSSVAGVALPS 1500
             A++P   GGA   A GA  + A A  G+G  A  A            ++S    A P+
Sbjct:  340  AATPGAAGGAVAAAAGGAAPASGASATVGTGGDAGCAAK-------SDDMASADRSATPA 392

Query: 1499  VAGVALLSVTGVTLPSVAGVMLPSVAGVTLPSVAGVALPSVAGVALRSAGATLSLFAARA 1320
                      GA  + G   P+  G + P+  G    P+     A P+    G
Sbjct:  393  TDGSATPATDGSVTPATDGSITPATDGSVTPATDRSATPATDG---------------R 436

Query: 1319  ASPSGAEVAPLAAAAVAPPAAPGVAV---SVAEADWAA 1215
             A+P+  E     AA + A PAA   A    +VA+ D A
Sbjct:  437  ATPATEESTVPAAQSSAAPAAKAAATPEPAVAQPDSTA 474

>gi|7521914|pir||T30814 calmodulin-binding protein kinase - Fugu
              rubripes
 emb|CAA09101.1| (AJ010348) calmodulin binding protein kinase [Fugu rubripes]
          Length = 421

Score =  598 bits (1526), Expect = e-170
 Identities = 296/391 (75%), Positives = 332/391 (84%), Gaps = 2/391 (0%)
 Frame = +1

Query:  211  MPFGCVTLGDKKNYNQPSEVTDRYDLGQVIKTEEFCEIFRAKDKTTGKLHTCKKFQKRDG 390
             MPFGC+TLG+KK+YN PSEVTD+YDLGQV+K+EEFCEIFRAKD+ T K++TCKKF K+DG
Sbjct:    1  MPFGCLTLGEKKDYNSPSEVTDKYDLGQVVKSEEFCEIFRAKDRNTLKMYTCKKFNKKDG 60

Query:  391  RKVRKAAKNEIGILKMVKHPNILQLVDVFVTRKEYFIFLELATGREVFDWILDQGYYSER 570
             RKVRKAAKNEI ILKMVKH NILQLVD F T+KEYFIFLELATGREVFDWILDQGYYSER
Sbjct:   61  RKVRKAAKNEIMILKMVKHHNILQLVDAFETKKEYFIFLELATGREVFDWILDQGYYSER 120

Query:  571  DTSNVVRQVLEAVAYLHSLKIVHRNLKLENLVYYNRLKNSKIVISDFHLAKLENGLIKEP 750
             DTSNV+RQVLEAVAYLHSLKIVHRNLK  NLVY+NRLK+SKIVISDF LAKLENGLIK+P
Sbjct:  121  DTSNVMRQVLEAVAYLHSLKIVHRNLK--NLVYFNRLKHSKIVISDFQLAKLENGLIKDP 178

Query:  751  CGTPEYLAPEVVGRQRYGRPVDCWAIGVIMYILLSGNPPFYEEVEEDDYENHDKNLFRKI 930
             CGTPEYLAPEV+GRQRYGRPVDCWAIGVIMYILLSGNPPFY++ +E+D ++ DKNLF KI
Sbjct:  179  CGTPEYLAPEVIGRQRYGRPVDCWAIGVIMYILLSGNPPFYDDGDEEDSDSRDKNLFLKI 238

Query:  931  LAGDYEFDSPYWDDISQAAKDLVTRLMEVEQDQRITAEEAISHEWISGNAASDKNIKDGV 1110
             L+GDYEFDSPYWDDIS +AK LV  LMEV+QDQR+TA+EAI+HEWISGNAASDKNIKDGV
Sbjct:  239  LSGDYEFDSPYWDDISDSAKTLVASLMEVDQDQRLTAQEAIAHEWISGNAASDKNIKDGV 298
```

FIGURE 2C

```
Query: 1111 CAQIEKNFARAKWKKAVRVTTLMKRLRAPEQSSTAAAQSASAT--DTATPGAAGGATAAA 1284
             CAQIEKNFA+AKWKKAVRVTTLMKRLRA EQ  T A+  A+         P    GG+  AA
Sbjct:  299 CAQIEKNFAKAKWKKAVRVTTLMKRLRASEQGDTGASGLAAGATGGPPDPNMPGGSLLAA 358

Query: 1285 ASGATSAPEGDAARAAKSDNVAPADRSATPA 1377
                     + + A S+  A A  S  P+
Sbjct:  359 -----------SIKTALSEKAADAQTSTIPS 378

>gi|3122310|sp|Q63450|KCC1_RAT CALCIUM/CALMODULIN-DEPENDENT PROTEIN
             KINASE TYPE I (CAM KINASE I)
 pir||S50193 Ca2+/calmodulin-dependent protein kinase (EC 2.7.1.123) I - rat
 gb|AAA66944.1| (L26288) CaM-like protein kinase [Rattus norvegicus]
 prf||2024225A Ca/calmodulin protein kinase I [Rattus norvegicus]
          Length = 374

Score =  310 bits (787), Expect = 4e-83
 Identities = 156/357 (43%), Positives = 226/357 (62%), Gaps = 4/357 (1%)
 Frame = +1

Query:  250 YNQPSEVTDRYDLGQVIKTEEFCEIFRAKDKTTGKLHTCKKFQKRDGRKVRKAAKNEIGI 429
             + Q  ++ D YD   V+ T  F E+   A+DK T KL    K  K+        + +NEI +
Sbjct:   10 WKQAEDIRDIYDFRDVLGTGAFSEVILAEDKRTQKLVAIKCIAKKALEGKEGSMENEIAV 69

Query:  430 LKMVKHPNILQLVDVFVTRKEYFIFLELATGREVFDWILDQGYYSERDTSNVVRQVLEAV 609
             L   +KHPNI+  L D++  +      ++ ++L +G E+FD I+++G+Y+ERD S ++  QVL+AV
Sbjct:   70 LHKIKHPNIVALDDIYESGGHLYLIMQLVSGGELFDRIVEKGFYTERDASRLIFQVLDAV 129

Query:  610 AYLHSLKIVHRNLKLENLVYYNRLKNSKIVISDFHLAKLEN--GLIKEPCGTPEYLAPEV 783
             YLH L  IVHR+LK ENL+YY+   ++SKI+ISDF L+K+E+       CGTP Y+APEV
Sbjct:  130 KYLHDLGIVHRDLKPENLLYYSLDEDSKIMISDFGLSKMEDPGSVLSTACGTPGYVAPEV 189

Query:  784 VGRQRYGRPVDCWAIGVIMYILLSGNPPFYEEVEEDDYENHDKNLFRKILAGDYEFDSPY 963
             + ++ Y +  VDCW+IGVI YILL G PPFY+E           +D  LF +IL  +YEFDSPY
Sbjct:  190 LAQKPYSKAVDCWSIGVIAYILLCGYPPFYDE---------NDAKLFEQILKAEYEFDSPY 241

Query:  964 WDDISQAAKDLVTRLMEVEQDQRITAEEAISHEWISGNAASDKNIKDGVCAQIEKNFARA 1143
             WDDIS +AKD +   LME +   ++R T E+A+ H WI+G+  A DKNI     V QI+KNFA++
Sbjct:  242 WDDISDSAKDFIRHLMEKDPEKRFTCEQALQHPWIAGDTALDKNIHQSVSEQIKKNFAKS 301

Query: 1144 KWKKAVRVTTLMKRLRAPE--QSSTAAAQSASATDTATPGAAGGATAAAASGATSAP 1308
             KWK+A   T +++ +R +         S    Q+AS +      TP A G A              P
Sbjct:  302 KWKQAFNATAVVRHMRKLQLGTSQEGQGQTASHGELLTPTAGGPAAGCCCRDCCVEP 358

>gi|4502553|ref|NP_003647.1| calcium/calmodulin-dependent protein
             kinase I [Homo sapiens]
 sp|Q14012|KCC1_HUMAN CALCIUM/CALMODULIN-DEPENDENT PROTEIN KINASE TYPE I (CAM KINASE I)
 pir||S57347 Ca2+/calmodulin-dependent protein kinase (EC 2.7.1.123) I - human
 gb|AAA99458.1| (L41816) cam kinase I [Homo sapiens]
          Length = 370

Score =  309 bits (784), Expect = 9e-83
 Identities = 156/357 (43%), Positives = 225/357 (62%), Gaps = 4/357 (1%)
 Frame = +1
```

FIGURE 2D

```
Query: 250   YNQPSEVTDRYDLGQVIKTEEFCEIFRAKDKTTGKLHTCKKFQKRDGRKVRKAAKNEIGI 429
             + Q  ++ D YD   V+ T  F E+  A+DK T KL    K   K+        + +NEI +
Sbjct: 10    WKQAEDIRDIYDFRDVLGTGAFSEVILAEDKRTQKLVAIKCIAKEALEGKEGSMENEIAV 69

Query: 430   LKMVKHPNILQLVDVFVTRKEYFIFLELATGREVFDWILDQGYYSERDTSNVVRQVLEAV 609
             L  +KHPNI+ L D++ +       ++ ++L +G E+FD  I+++G+Y+ERD S ++ QVL+AV
Sbjct: 70    LHKIKHPNIVALDDIYESGGHLYLIMQLVSGGELFDRIVEKGFYTERDASRLIFQVLDAV 129

Query: 610   AYLHSLKIVHRNLKLENLVYYNRLKNSKIVISDFHLAKLEN--GLIKEPCGTPEYLAPEV 783
                YLH L IVHR+LK ENL+YY+  ++SKI+ISDF L+K+E+    ++    CGTP Y+APEV
Sbjct: 130   KYLHDLGIVHRDLKPENLLYYSLDEDSKIMISDFGLSKMEDPGSVLSTACGTPGYVAPEV 189

Query: 784   VGRQRYGRPVDCWAIGVIMYILLSGNPPFYEEVEEDDYENHDKNLFRKILAGDYEFDSPY 963
             + ++  Y + VDCW+IGVI YILL G PPFY+E         +D  LF +IL +YEFDSPY
Sbjct: 190   LAQKPYSKAVDCWSIGVIAYILLCGYPPFYDE--------NDAKLFEQILKAEYEFDSPY 241

Query: 964   WDDISQAAKDLVTRLMEVEQDQRITAEEAISHEWISGNAASDKNIKDGVCAQIEKNFARA 1143
             WDDIS +AKD +  LME + ++R T E+A+ H WI+G+ A DKNI   V  QI+KNFA++
Sbjct: 242   WDDISDSAKDFIRHLMEKDPEKRFTCEQALQHPWIAGDTALDKNIHQSVSEQIKKNFAKS 301

Query: 1144  KWKKAVRVTTLMKRLRAPE--QSSTAAAQSASATDTATPGAAGGATAAAASGATSAP 1308
             KWK+A     T +++ +R  +    S    Q+AS +  TP A G A              P
Sbjct: 302   KWKQAFNATAVVRHMRKLQLGTSQEGQGQTASHGELLTPVAGGPAAGCCCRDCCVEP 358

>gi|3114436|pdb|1A06|   Calmodulin-Dependent Protein Kinase From Rat
         Length = 332

Score =  303 bits (768), Expect = 7e-81
 Identities = 146/316 (46%), Positives = 213/316 (67%), Gaps = 2/316 (0%)
 Frame = +1

Query: 250   YNQPSEVTDRYDLGQVIKTEEFCEIFRAKDKTTGKLHTCKKFQKRDGRKVRKAAKNEIGI 429
             + Q  ++ D YD   V+ T  F E+  A+DK T KL    K   K+        + +NEI +
Sbjct: 10    WKQAEDIRDIYDFRDVLGTGAFSEVILAEDKRTQKLVAIKCIAKKALEGKEGSMENEIAV 69

Query: 430   LKMVKHPNILQLVDVFVTRKEYFIFLELATGREVFDWILDQGYYSERDTSNVVRQVLEAV 609
             L  +KHPNI+ L D++ +       ++ ++L +G E+FD  I+++G+Y+ERD S ++ QVL+AV
Sbjct: 70    LHKIKHPNIVALDDIYESGGHLYLIMQLVSGGELFDRIVEKGFYTERDASRLIFQVLDAV 129

Query: 610   AYLHSLKIVHRNLKLENLVYYNRLKNSKIVISDFHLAKLEN--GLIKEPCGTPEYLAPEV 783
                YLH L IVHR+LK ENL+YY+  ++SKI+ISDF L+K+E+    ++    CGTP Y+APEV
Sbjct: 130   KYLHDLGIVHRDLKPENLLYYSLDEDSKIMISDFGLSKMEDPGSVLSTACGTPGYVAPEV 189

Query: 784   VGRQRYGRPVDCWAIGVIMYILLSGNPPFYEEVEEDDYENHDKNLFRKILAGDYEFDSPY 963
             + ++  Y + VDCW+IGVI YILL G PPFY+E         +D  LF +IL +YEFDSPY
Sbjct: 190   LAQKPYSKAVDCWSIGVIAYILLCGYPPFYDE--------NDAKLFEQILKAEYEFDSPY 241

Query: 964   WDDISQAAKDLVTRLMEVEQDQRITAEEAISHEWISGNAASDKNIKDGVCAQIEKNFARA 1143
             WDDIS +AKD +  LME + ++R T E+A+ H WI+G+ A DKNI   V  QI+KNFA++
Sbjct: 242   WDDISDSAKDFIRHLMEKDPEKRFTCEQALQHPWIAGDTALDKNIHQSVSEQIKKNFAKS 301

Query: 1144  KWKKAVRVTTLMKRLR 1191
              KWK+A     T +++ +R
Sbjct: 302   KWKQAFNATAVVRHMR 317
```

FIGURE 2E

>gi|406113|gb|AAA19670.1| (L24907) protein kinase I [Rattus
    norvegicus]
        Length = 332

Score =  299 bits (758), Expect = 1e-79
Identities = 146/316 (46%), Positives = 212/316 (66%), Gaps = 2/316 (0%)
Frame = +1

Query: 250   YNQPSEVTDRYDLGQVIKTEEFCEIFRAKDKTTGKLHTCKKFQKRDGRKVRKAAKNEIGI 429
             + Q  ++ D YD   V+ T  F E+ A+DK T KL    K   K+       + +NEI +
Sbjct: 10    WKQAEDIRDIYDFRDVLGTGAFSEVILAEDKRTQKLVAIKCIAKKALEGKEGSMENEIAV 69

Query: 430   LKMVKHPNILQLVDVFVTRKEYFIFLELATGREVFDWILDQGYYSERDTSNVVRQVLEAV 609
             L  +KHPNI+ L D++ +      ++ ++L +G E+FD I+++G Y+ERD S ++ QVL+AV
Sbjct: 70    LHKIKHPNIVALDDIYESGGHLYLIMQLVSGGELFDRIVEKGGYTERDRSRLIFQVLDAV 129

Query: 610   AYLHSLKIVHRNLKLENLVYYNRLKNSKIVISDFHLAKLEN--GLIKEPCGTPEYLAPEV 783
               YLH L  IVHR+LK ENL+YY+   ++SKI+ISDF L+K+E+    ++   CGTP Y+APEV
Sbjct: 130   KYLHDLGIVHRDLKPENLLYYSLDEDSKIMISDFGLSKMEDPGSVLSTACGTPGYVAPEV 189

Query: 784   VGRQRYGRPVDCWAIGVIMYILLSGNPPFYEEVEEDDYENHDKNLFRKILAGDYEFDSPY 963
             + ++  Y + VDCW+IGVI YILL G PPFY+E         +D  LF +IL +YEFDSPY
Sbjct: 190   LAQKPYSKAVDCWSIGVIAYILLCGYPPFYDE--------NDAKLFEQILKAEYEFDSPY 241

Query: 964   WDDISQAAKDLVTRLMEVEQDQRITAEEAISHEWISGNAASDKNIKDGVCAQIEKNFARA 1143
             WDDIS +AKD +  LME + ++R T E+A+  H WI+G+ A DKNI   V  QI+KNFA++
Sbjct: 242   WDDISDSAKDFIRHLMEKDPEKRFTCEQALQHPWIAGDTALDKNIHQSVSEQIKKNFAKS 301

Query: 1144  KWKKAVRVTTLMKRLR 1191
             KWK+A   T +++ +R
Sbjct: 302   KWKQAFNRTAVVRHMR 317

>gi|9966875|ref|NP_065130.1| CamKI-like protein kinase [Homo sapiens]
  gb|AAG00534.1|AF286366_1 (AF286366) CamKI-like protein kinase [Homo sapiens]
        Length = 357

Score =  299 bits (757), Expect = 1e-79
Identities = 142/332 (42%), Positives = 221/332 (65%), Gaps = 2/332 (0%)
Frame = +1

Query: 256   QPSEVTDRYDLGQVIKTEEFCEIFRAKDKTTGKLHTCKKFQKRDGRKVRKAAKNEIGILK 435
             Q ++   ++ + +  T F E+ A++K TGKL    K  K+     +  +NEI +L+
Sbjct: 15    QAEDIKKIFEFKETLGTGAFSEVVLAEEKATGKLFAVKCIPKKALKGKESSIENEIAVLR 74

Query: 436   MVKHPNILQLVDVFVTRKEYFIFLELATGREVFDWILDQGYYSERDTSNVVRQVLEAVAY 615
             +KH NI+ L D++ +      ++ ++L +G E+FD I+++G+Y+E+D S  ++RQVL+AV Y
Sbjct: 75    KIKHENIVALEDIYESPNHLYLVMQLVSGGELFDRIVEKGFYTEKDASTLIRQVLDAVYY 134

Query: 616   LHSLKIVHRNLKLENLVYYNRLKNSKIVISDFHLAKLE--NGLIKEPCGTPEYLAPEVVG 789
             LH +  IVHR+LK ENL+YY++ +    SKI+ISDF L+K+E     ++   CGTP Y+APEV+
Sbjct: 135   LHRMGIVHRDLKPENLLYYSQDEESKIMISDFGLSKMEGKGDVMSTACGTPGYVAPEVLA 194

Query: 790   RQRYGRPVDCWAIGVIMYILLSGNPPFYEEVEEDDYENHDKNLFRKILAGDYEFDSPYWD 969
             ++  Y + VDCW+IGVI YILL G PPFY+E         +D  LF +IL +YEFDSPYWD
Sbjct: 195   QKPYSKAVDCWSIGVIAYILLCGYPPFYDE--------NDSKLFEQILKAEYEFDSPYWD 246

FIGURE 2F

```
Query:  970  DISQAAKDLVTRLMEVEQDQRITAEEAISHEWISGNAASDKNIKDGVCAQIEKNFARAKW 1149
             DIS +AKD +  LME + ++R T E+A  H WI+G+ A +KNI + V AQI KNFA++KW
Sbjct:  247  DISDSAKDFIRNLMEKDPNKRYTCEQAARHPWIAGDTALNKNIHESVSAQIRKNFAKSKW 306

Query: 1150  KKAVRVTTLMKRLRAPEQSSTAAAQSASATDT 1245
             ++A  T +++ +R       S+  + +AS + +
Sbjct:  307  RQAFNATAVVRHMRKLHLGSSLDSSNASVSSS 338

>gi|3893099|emb|CAA76937.1| (Y17917) calcium/calmodulin dependent
          protein kinase I [Drosophila melanogaster]
 gb|AAF59343.1| (AE003844) CaMKI gene product [alt 2] [Drosophila melanogaster]
          Length = 405

Score =  288 bits (729), Expect = 3e-76
 Identities = 152/388 (39%), Positives = 243/388 (62%), Gaps = 21/388 (5%)
 Frame = +1

Query:  238  DKKNYNQPSEVTDRYDLGQVIKTEEFCEIFRAKDKTT-GKLHTCKKFQKRDGRKVRKAAK 414
             D K  N+   + ++Y+L ++  T  F E+ A+ K + G+     K  K+ +  ++ +
Sbjct:   17  DLKELNKQVSIEEKYNLHGLLGTGAFSEVRLAESKDSPGEHFAVKIIDKKALKGKEESLE 76

Query:  415  NEIGILKM---------------VKHPNILQLVDVFVTRKEYFIFLELATGREVFDWILD 549
             NEI +L+                + HPNI+QL++ +  + ++ ++ +EL TG E+FD I++
Sbjct:   77  NEIRVLRRFSANHFDGKCLNGTRLTHPNIVQLLETYEDKSKVYLVMELVTGGELFDRIVE 136

Query:  550  QGYYSERDTSNVVRQVLEAVAYLHSLKIVHRNLKLENLVYYNRLKNSKIVISDFHLAKLE 729
             +G Y+E+D S+++RQ+LEAV Y+H   +VHR+LK ENL+YY+    +SKI+ISDF L+K+E
Sbjct:  137  KGSYTEKDASHLIRQILEAVDYMHEQGVVHRDLKPENLLYYSPDDDSKIMISDFGLSKME 196

Query:  730  N-GLIKEPCGTPEYLAPEVVGRQRYGRPVDCWAIGVIMYILLSGNPPFYEEVEEDDYENH 906
             +  G++    CGTP  Y+APEV+ ++ YG+ VD W+IGVI YILL G PPFY+E       +
Sbjct:  197  DSGIMATACGTPGYVAPEVLAQKPYGKAVDVWSIGVISYILLCGYPPFYDE--------N 248

Query:  907  DKNLFRKILAGDYEFDSPYWDDISQAAKDLVTRLMEVEQDQRITAEEAISHEWISGNAAS 1086
             D NLF +IL GD+EFDSPYWD+IS++AK  +  LM V ++R T ++A+ H WISGN AS
Sbjct:  249  DANLFAQILKGDFEFDSPYWDEISESAKHFIKNLMCVTVEKRYTCKQALGHAWISGNEAS 308

Query: 1087  DKNIKDGVCAQIEKNFARAKWKKAVRVTTLMKRLRAPEQSSTAAA----QSASATDTATP 1254
             +NI   V Q++KNFA+++WK+A   T+++++   +S + A     ++S D+ TP
Sbjct:  309  SRNIHGTVSEQLKKNFAKSRWKQAYYAATVIRQMQRMALNSNSNANFDSSNSSNQDSTTP 368

Query: 1255  GAAGGATAAAASGATSAPEGDAARAAKS 1338
             AA GA  +    + ++ A       KS
Sbjct:  369  TAATGAWTSNVLSSQQSVQSHAQEMNKS 396

>gi|4007153|emb|CAA19296.1| (AL023754) dJ272L16.1 (Rat Ca2+/Calmodulin
          dependent Protein Kinase LIKE protein) [Homo sapiens]
          Length = 460

Score =  286 bits (724), Expect = 1e-75
 Identities = 157/408 (38%), Positives = 233/408 (56%), Gaps = 5/408 (1%)
 Frame = +1

Query:  256  QPSEVTDRYDLGQVIKTEEFCEIFRAKDKTTGKLHTCKKFQKRDGRKVRKAAKNEIGILK 435
             Q + +    +V+ +   F E+F  K + TGKL    K  +K   +  + +NEI +LK
Sbjct:   15  QTTNIRKTFIFMEVLGSGAFSEVFLVKQRLTGKLFALKCIKKSPAFR-DSSLENEIAVLK 73
```

FIGURE 2G

```
Query: 436   MVKHPNILQLVDVFVTRKEYFIFLELATGREVFDWILDQGYYSERDTSNVVRQVLEAVAY 615
              +KH NI+ L D++ +    Y++ ++L +G E+FD IL++G Y+E+D S V++QVL AV Y
Sbjct: 74    KIKHENIVTLEDIYESTTHYYLVMQLVSGGELFDRILERGVYTEKDASLVIQQVLSAVKY 133

Query: 616   LHSLKIVHRNLKLENLVYYNRLKNSKIVISDFHLAKLE-NGLIKEPCGTPEYLAPEVVGR 792
              LH   IVHR+LK ENL+Y   +NSKI+I+DF L+K+E NG++   CGTP Y+APEV+ +
Sbjct: 134   LHENGIVHRDLKPENLLYLTPEENSKIMITDFGLSKMEQNGIMSTACGTPGYVAPEVLAQ 193

Query: 793   QRYGRPVDCWAIGVIMYILLSGNPPFYEEVEEDDYENHDKNLFRKILAGDYEFDSPYWDD 972
              + Y + VDCW+IGVI YILL G PPFYEE E        LF KI  G YEF+SP+WDD
Sbjct: 194   KPYSKAVDCWSIGVITYILLCGYPPFYEETE--------SKLFEKIKEGYYEFESPFWDD 245

Query: 973   ISQAAKDLVTRLMEVEQDQRITAEEAISHEWISGNAASDKNIKDGVCAQIEKNFARAKWK 1152
              IS++AKD + L+E + ++R T E+A+SH WI GN A  ++I   V  QI+KNFA++KW+
Sbjct: 246   ISESAKDFICHLLEKDPNERYTCEKALSHPWIDGNTALHRDIYPSVSLQIQKNFAKSKWR 305

Query: 1153  KAVRVTTLMKRLRAPEQS--STAAAQSASATDTATPGAAGGATAAAASGATSAPEGDAAR 1326
              +A    ++ +R   + S       T +    ++     T AP  D +
Sbjct: 306   QAFNAAAVVHHMRKLHMNLHSPGVRPEVENRPPETQASETSRPSSPEITITEAPVLDHSV 365

Query: 1327  AAKSDNVAPADRSATPATDG--SATPATDGSVTPATDGSITPATDGSV 1464
              A +   P    P   G    +GS+     S+ P   GS+
Sbjct: 366   ALPALTQLPCQHGRRPTAPGGRSLNCLVNGSL--HISSSLVPMHQGSL 411

>gi|4678722|emb|CAB41259.1| (AL049688) hypothetical protein [Homo
            sapiens]
          Length = 481

Score = 286 bits (724), Expect = 1e-75
 Identities = 157/408 (38%), Positives = 233/408 (56%), Gaps = 5/408 (1%)
 Frame = +1

Query: 256   QPSEVTDRYDLGQVIKTEEFCEIFRAKDKTTGKLHTCKKFQKRDGRKVRKAAKNEIGILK 435
              Q + +    +V+ +    F E+F  K + TGKL    K  +K +   + +NEI +LK
Sbjct: 20    QTTNIRKTFIFMEVLGSGAFSEVFLVKQRLTGKLFALKCIKKSPAFR-DSSLENEIAVLK 78

Query: 436   MVKHPNILQLVDVFVTRKEYFIFLELATGREVFDWILDQGYYSERDTSNVVRQVLEAVAY 615
              +KH NI+ L D++ +    Y++ ++L +G E+FD IL++G Y+E+D S V++QVL AV Y
Sbjct: 79    KIKHENIVTLEDIYESTTHYYLVMQLVSGGELFDRILERGVYTEKDASLVIQQVLSAVKY 138

Query: 616   LHSLKIVHRNLKLENLVYYNRLKNSKIVISDFHLAKLE-NGLIKEPCGTPEYLAPEVVGR 792
              LH   IVHR+LK ENL+Y   +NSKI+I+DF L+K+E NG++   CGTP Y+APEV+ +
Sbjct: 139   LHENGIVHRDLKPENLLYLTPEENSKIMITDFGLSKMEQNGIMSTACGTPGYVAPEVLAQ 198

Query: 793   QRYGRPVDCWAIGVIMYILLSGNPPFYEEVEEDDYENHDKNLFRKILAGDYEFDSPYWDD 972
              + Y + VDCW+IGVI YILL G PPFYEE E        LF KI  G YEF+SP+WDD
Sbjct: 199   KPYSKAVDCWSIGVITYILLCGYPPFYEETE--------SKLFEKIKEGYYEFESPFWDD 250

Query: 973   ISQAAKDLVTRLMEVEQDQRITAEEAISHEWISGNAASDKNIKDGVCAQIEKNFARAKWK 1152
              IS++AKD + L+E + ++R T E+A+SH WI GN A  ++I   V  QI+KNFA++KW+
Sbjct: 251   ISESAKDFICHLLEKDPNERYTCEKALSHPWIDGNTALHRDIYPSVSLQIQKNFAKSKWR 310

Query: 1153  KAVRVTTLMKRLRAPEQS--STAAAQSASATDTATPGAAGGATAAAASGATSAPEGDAAR 1326
              +A    ++ +R   + S       T +    ++     T AP  D +
Sbjct: 311   QAFNAAAVVHHMRKLHMNLHSPGVRPEVENRPPETQASETSRPSSPEITITEAPVLDHSV 370
```

FIGURE 2H

```
Query: 1327  AAKSDNVAPADRSATPATDG--SATPATDGSVTPATDGSITPATDGSV 1464
             A +   P      P  G S   +GS+      S+ P   GS+
Sbjct:  371  ALPALTQLPCQHGRRPTAPGGRSLNCLVNGSL--HISSSLVPMHQGSL 416

>gi|2143639|pir||I56542 calmodulin-binding protein - rat
 gb|AAA16633.1| (L22557) calmodulin-binding protein [Rattus norvegicus]
        Length = 504

Score =  929 bits (2375), Expect = 0.0
 Identities = 468/509 (91%), Positives = 473/509 (91%), Gaps = 8/509 (1%)
 Frame = +1

Query:  211  MPFGCVTLGDKKNYNQPSEVTDRYDLGQVIKTEEFCEIFRAKDKTTGKLHTCKKFQKRDG 390
             MPFGCVTLGDKKNYNQPSEVTDRYDLGQV+KTEEFCEIFRAKDKTTGKLHTCKKFQKRDG
Sbjct:    1  MPFGCVTLGDKKNYNQPSEVTDRYDLGQVVKTEEFCEIFRAKDKTTGKLHTCKKFQKRDG 60

Query:  391  RKVRKAAKNEIGILKMVKHPNILQLVDVFVTRKEYFIFLELATGREVFDWILDQGYYSER 570
             RKVRKAAKNEIGILKMVKHPNILQLVDVFVTRKEYFIFLELATGREVFDWILDQGYYSER
Sbjct:   61  RKVRKAAKNEIGILKMVKHPNILQLVDVFVTRKEYFIFLELATGREVFDWILDQGYYSER 120

Query:  571  DTSNVVRQVLEAVAYLHSLKIVHRNLKLENLVYYNRLKNSKIVISDFHLAKLENGLIKEP 750
             DTSNVVRQVLEAVAYLHSLKIVHRNLKLENLVYYNRLKNSKIVISDFHLAKLENGLIKEP
Sbjct:  121  DTSNVVRQVLEAVAYLHSLKIVHRNLKLENLVYYNRLKNSKIVISDFHLAKLENGLIKEP 180

Query:  751  CGTPEYLAPEVVGRQRYGRPVDCWAIGVIMYILLSGNPPFYEEVEEDDYENHDKNLFRKI 930
             CGTPEYLAPEVVGRQRYGRPVDCWAIGVIMYILLSGNPPFYEEVEEDDYENHDKNLFRKI
Sbjct:  181  CGTPEYLAPEVVGRQRYGRPVDCWAIGVIMYILLSGNPPFYEEVEEDDYENHDKNLFRKI 240

Query:  931  LAGDYEFDSPYWDDISQAAKDLVTRLMEVEQDQRITAEEAISHEWISGNAASDKNIKDGV 1110
             LAGDYEFDSPYWDDISQAAKDLVTRLMEVEQDQRITAEEAISHEWISGNAASDKNIKDGV
Sbjct:  241  LAGDYEFDSPYWDDISQAAKDLVTRLMEVEQDQRITAEEAISHEWISGNAASDKNIKDGV 300

Query: 1111  CAQIEKNFARAKWKKAVRVTTLMKRLRAPEQSSTAAAQSASATDTATPGAAGGATAAAAS 1290
             CAQIEKNFARAKWKKAVRVTTLMKRLRAPEQS TAA      +D ATPGAAGGA AAAA
Sbjct:  301  CAQIEKNFARAKWKKAVRVTTLMKRLRAPEQSGTAA-----TSDAATPGAAGGAVAAAAG 355

Query: 1291  G--------ATSAPEGDAARAAKSDNVAPADRSATPATDGSATPATDGSVTPATDGSITP 1446
             G        AT   GDA   AAKSD++A ADRSATPATDGSATPATDGSVTPATDGSITP
Sbjct:  356  GAAPASGASATVGTGGDAGCAAKSDDMASADRSATPATDGSATPATDGSVTPATDGSITP 415

Query: 1447  ATDGSVTPVTDRSATPATDGRATPATEESTVPTTQSSAMLATKAAATPEPAMAQPDSTAP 1626
             ATDGSVTP TDRSATPATDGRATPATEESTVP  QSSA  A KAAATPEPA+AQPDSTA
Sbjct:  416  ATDGSVTPATDRSATPATDGRATPATEESTVPAAQSSAAPAAKAAATPEPAVAQPDSTAL 475

Query: 1627  EGATGQAPPSSKGEEAAGYAQESQREEAS 1713
             EGATGQAPPSSKGEEA G AQESQR E S
Sbjct:  476  EGATGQAPPSSKGEEATGCAQESQRVETS 504

Score = 34.4 bits (77), Expect = 7.1
 Identities = 42/158 (26%), Positives = 60/158 (37%), Gaps = 5/158 (3%)
 Frame = -3

Query: 1673  ASSPLLEGGAWPVAPSGAVLSGWAIA--GSGVAAALVASMALLWVVGTVLSSVAGVALPS 1500
             A++P   GGA    A GA + A G+G A A           ++S   A P+
Sbjct:  340  AATPGAAGGAVAAAAGGAAPASGASATVGTGGDAGCAAK-------SDDMASADRSATPA 392
```

FIGURE 2I

```
Query:  1499  VAGVALLSVTGVTLPSVAGVMLPSVAGVTLPSVAGVALPSVAGVALRSAGATLSLFAARA  1320
               G A  +  G    P+   G + P+   G     P+    A P+     G
Sbjct:   393  TDGSATPATDGSVTPATDGSITPATDGSVTPATDRSATPATDG---------------R  436

Query:  1319  ASPSGAEVAPLAAAAVAPPAAPGVAV---SVAEADWAA  1215
               A+P+   E     AA + A PAA   A    +VA+ D A
Sbjct:   437  ATPATEESTVPAAQSSAAPAAKAAATPEPAVAQPDSTA  474

>gi|7521914|pir||T30814 calmodulin-binding protein kinase - Fugu
              rubripes
  emb|CAA09101.1| (AJ010348) calmodulin binding protein kinase [Fugu rubripes]
          Length = 421

Score =  598 bits (1526), Expect = e-170
 Identities = 296/391 (75%), Positives = 332/391 (84%), Gaps = 2/391 (0%)
 Frame = +1

Query:   211  MPFGCVTLGDKKNYNQPSEVTDRYDLGQVIKTEEFCEIFRAKDKTTGKLHTCKKFQKRDG  390
              MPFGC+TLG+KK+YN PSEVTD+YDLGQV+K+EEFCEIFRAKD+ T K++TCKKF K+DG
Sbjct:     1  MPFGCLTLGEKKDYNSPSEVTDKYDLGQVVKSEEFCEIFRAKDRNTLKMYTCKKFNKKDG   60

Query:   391  RKVRKAAKNEIGILKMVKHPNILQLVDVFVTRKEYFIFLELATGREVFDWILDQGYYSER  570
              RKVRKAAKNEI ILKMVKH NILQLVD F T+KEYFIFLELATGREVFDWILDQGYYSER
Sbjct:    61  RKVRKAAKNEIMILKMVKHHNILQLVDAFETKKEYFIFLELATGREVFDWILDQGYYSER  120

Query:   571  DTSNVVRQVLEAVAYLHSLKIVHRNLKLENLVYYNRLKNSKIVISDFHLAKLENGLIKEP  750
              DTSNV+RQVLEAVAYLHSLKIVHRNLK  NLVY+NRLK+SKIVISDF LAKLENGLIK+P
Sbjct:   121  DTSNVMRQVLEAVAYLHSLKIVHRNLK--NLVYFNRLKHSKIVISDFQLAKLENGLIKDP  178

Query:   751  CGTPEYLAPEVVGRQRYGRPVDCWAIGVIMYILLSGNPPFYEEVEEDDYENHDKNLFRKI  930
              CGTPEYLAPEV+GRQRYGRPVDCWAIGVIMYILLSGNPPFY++  +E+D ++ DKNLF KI
Sbjct:   179  CGTPEYLAPEVIGRQRYGRPVDCWAIGVIMYILLSGNPPFYDDGDEEDSDSRDKNLFLKI  238

Query:   931  LAGDYEFDSPYWDDISQAAKDLVTRLMEVEQDQRITAEEEAISHEWISGNAASDKNIKDGV  1110
              L+GDYEFDSPYWDDIS +AK LV  LMEV+QDQR+TA+EAI+HEWISGNAASDKNIKDGV
Sbjct:   239  LSGDYEFDSPYWDDISDSAKTLVASLMEVDQDQRLTAQEAIAHEWISGNAASDKNIKDGV  298

Query:  1111  CAQIEKNFARAKWKKAVRVTTLMKRLRAPEQSSTAAAQSASAT--DTATPGAAGGATAAA  1284
              CAQIEKNFA+AKWKKAVRVTTLMKRLRA EQ  T A+   A+            P   GG+  AA
Sbjct:   299  CAQIEKNFAKAKWKKAVRVTTLMKRLRASEQGDTGASGLAAGATGGPPDPNMPGGSLLAA  358

Query:  1285  ASGATSAPEGDAARAAKSDNVAPADRSATPA  1377
               + + A S+  A A  S   P+
Sbjct:   359  -----------SIKTALSEKAADAQTSTIPS  378

>gi|3122310|sp|Q63450|KCC1_RAT CALCIUM/CALMODULIN-DEPENDENT PROTEIN
              KINASE TYPE I (CAM KINASE I)
  pir||S50193 Ca2+/calmodulin-dependent protein kinase (EC 2.7.1.123) I - rat
  gb|AAA66944.1| (L26288) CaM-like protein kinase [Rattus norvegicus]
  prf||2024225A Ca/calmodulin protein kinase I [Rattus norvegicus]
          Length = 374

Score =  310 bits (787), Expect = 4e-83
 Identities = 156/357 (43%), Positives = 226/357 (62%), Gaps = 4/357 (1%)
 Frame = +1
```

FIGURE 2J

```
Query:  250  YNQPSEVTDRYDLGQVIKTEEFCEIFRAKDKTTGKLHTCKKFQKRDGRKVRKAAKNEIGI  429
             + Q  ++ D YD   V+ T  F E+  A+DK T KL    K    K+      + +NEI +
Sbjct:   10  WKQAEDIRDIYDFRDVLGTGAFSEVILAEDKRTQKLVAIKCIAKKALEGKEGSMENEIAV  69

Query:  430  LKMVKHPNILQLVDVFVTRKEYFIFLELATGREVFDWILDQGYYSERDTSNVVRQVLEAV  609
             L  +KHPNI+ L D++  +      ++ ++L +G E+FD I+++G+Y+ERD S ++ QVL+AV
Sbjct:   70  LHKIKHPNIVALDDIYESGGHLYLIMQLVSGGELFDRIVEKGFYTERDASRLIFQVLDAV  129

Query:  610  AYLHSLKIVHRNLKLENLVYYNRLKNSKIVISDFHLAKLEN--GLIKEPCGTPEYLAPEV  783
                 YLH L  IVHR+LK ENL+YY+  ++SKI+ISDF L+K+E+  ++    CGTP Y+APEV
Sbjct:  130  KYLHDLGIVHRDLKPENLLYYSLDEDSKIMISDFGLSKMEDPGSVLSTACGTPGYVAPEV  189

Query:  784  VGRQRYGRPVDCWAIGVIMYILLSGNPPFYEEVEEDDYENHDKNLFRKILAGDYEFDSPY  963
             +  ++  Y +  VDCW+IGVI YILL G PPFY+E         +D    LF +IL  +YEFDSPY
Sbjct:  190  LAQKPYSKAVDCWSIGVIAYILLCGYPPFYDE--------NDAKLFEQILKAEYEFDSPY  241

Query:  964  WDDISQAAKDLVTRLMEVEQDQRITAEEAISHEWISGNAASDKNIKDGVCAQIEKNFARA  1143
             WDDIS +AKD +  LME + ++R T E+A+ H WI+G+ A DKNI     V  QI+KNFA++
Sbjct:  242  WDDISDSAKDFIRHLMEKDPEKRFTCEQALQHPWIAGDTALDKNIHQSVSEQIKKNFAKS  301

Query: 1144  KWKKAVRVTTLMKRLRAPE--QSSTAAAQSASATDTATPGAAGGATAAAASGATSAP  1308
             KWK+A    T +++ +R +    S    Q+AS +   TP A G A             P
Sbjct:  302  KWKQAFNATAVVRHMRKLQLGTSQEGQGQTASHGELLTPTAGGPAAGCCCRDCCVEP  358

>gi|4502553|ref|NP_003647.1| calcium/calmodulin-dependent protein
             kinase I [Homo sapiens]
 sp|Q14012|KCC1_HUMAN CALCIUM/CALMODULIN-DEPENDENT PROTEIN KINASE TYPE I (CAM KINASE I)
 pir||S57347 Ca2+/calmodulin-dependent protein kinase (EC 2.7.1.123) I - human
 gb|AAA99458.1| (L41816) cam kinase I [Homo sapiens]
          Length = 370

Score =  309 bits (784), Expect = 9e-83
 Identities = 156/357 (43%), Positives = 225/357 (62%), Gaps = 4/357 (1%)
 Frame = +1

Query:  250  YNQPSEVTDRYDLGQVIKTEEFCEIFRAKDKTTGKLHTCKKFQKRDGRKVRKAAKNEIGI  429
             + Q  ++ D YD   V+ T  F E+  A+DK T KL    K    K       + +NEI +
Sbjct:   10  WKQAEDIRDIYDFRDVLGTGAFSEVILAEDKRTQKLVAIKCIAKEALEGKEGSMENEIAV  69

Query:  430  LKMVKHPNILQLVDVFVTRKEYFIFLELATGREVFDWILDQGYYSERDTSNVVRQVLEAV  609
             L  +KHPNI+ L D++  +      ++ ++L +G E+FD I+++G+Y+ERD S ++ QVL+AV
Sbjct:   70  LHKIKHPNIVALDDIYESGGHLYLIMQLVSGGELFDRIVEKGFYTERDASRLIFQVLDAV  129

Query:  610  AYLHSLKIVHRNLKLENLVYYNRLKNSKIVISDFHLAKLEN--GLIKEPCGTPEYLAPEV  783
                 YLH L  IVHR+LK ENL+YY+  ++SKI+ISDF L+K+E+  ++    CGTP Y+APEV
Sbjct:  130  KYLHDLGIVHRDLKPENLLYYSLDEDSKIMISDFGLSKMEDPGSVLSTACGTPGYVAPEV  189

Query:  784  VGRQRYGRPVDCWAIGVIMYILLSGNPPFYEEVEEDDYENHDKNLFRKILAGDYEFDSPY  963
             +  ++  Y +  VDCW+IGVI YILL G PPFY+E         +D    LF +IL  +YEFDSPY
Sbjct:  190  LAQKPYSKAVDCWSIGVIAYILLCGYPPFYDE--------NDAKLFEQILKAEYEFDSPY  241

Query:  964  WDDISQAAKDLVTRLMEVEQDQRITAEEAISHEWISGNAASDKNIKDGVCAQIEKNFARA  1143
             WDDIS +AKD +  LME + ++R T E+A+ H WI+G+ A DKNI     V  QI+KNFA++
Sbjct:  242  WDDISDSAKDFIRHLMEKDPEKRFTCEQALQHPWIAGDTALDKNIHQSVSEQIKKNFAKS  301
```

FIGURE 2K

```
Query: 1144  KWKKAVRVTTLMKRLRAPE--QSSTAAAQSASATDTATPGAAGGATAAAASGATSAP  1308
             KWK+A   T +++ +R +    S    Q+AS  + TP AG A           P
Sbjct: 302   KWKQAFNATAVVRHMRKLQLGTSQEGQGQTASHGELLTPVAGGPAAGCCCRDCCVEP  358

>gi|3114436|pdb|1A06|    Calmodulin-Dependent Protein Kinase From Rat
            Length = 332

Score =  303 bits (768), Expect = 7e-81
 Identities = 146/316 (46%), Positives = 213/316 (67%), Gaps = 2/316 (0%)
 Frame = +1

Query: 250   YNQPSEVTDRYDLGQVIKTEEFCEIFRAKDKTTGKLHTCKKFQKRDGRKVRKAAKNEIGI  429
             + Q  ++ D YD   V+ T  F E+  A+DK T KL    K   K+       + +NEI +
Sbjct: 10    WKQAEDIRDIYDFRDVLGTGAFSEVILAEDKRTQKLVAIKCIAKKALEGKEGSMENEIAV  69

Query: 430   LKMVKHPNILQLVDVFVTRKEYFIFLELATGREVFDWILDQGYYSERDTSNVVRQVLEAV  609
             L  +KHPNI+ L D++ +      ++ ++L +G E+FD I+++G+Y+ERD S ++ QVL+AV
Sbjct: 70    LHKIKHPNIVALDDIYESGGHLYLIMQLVSGGELFDRIVEKGFYTERDASRLIFQVLDAV  129

Query: 610   AYLHSLKIVHRNLKLENLVYYNRLKNSKIVISDFHLAKLEN--GLIKEPCGTPEYLAPEV  783
             YLH L  IVHR+LK ENL+YY+   ++SKI+ISDF L+K+E+    ++    CGTP Y+APEV
Sbjct: 130   KYLHDLGIVHRDLKPENLLYYSLDEDSKIMISDFGLSKMEDPGSVLSTACGTPGYVAPEV  189

Query: 784   VGRQRYGRPVDCWAIGVIMYILLSGNPPFYEEVEEDDYENHDKNLFRKILAGDYEFDSPY  963
             + ++ Y + VDCW+IGVI YILL G PPFY+E            +D  LF +IL  +YEFDSPY
Sbjct: 190   LAQKPYSKAVDCWSIGVIAYILLCGYPPFYDE--------NDAKLFEQILKAEYEFDSPY  241

Query: 964   WDDISQAAKDLVTRLMEVEQDQRITAEEAISHEWISGNAASDKNIKDGVCAQIEKNFARA  1143
             WDDIS +AKD + LME + ++R T E+A+ H WI+G+  A DKNI   V  QI+KNFA++
Sbjct: 242   WDDISDSAKDFIRHLMEKDPEKRFTCEQALQHPWIAGDTALDKNIHQSVSEQIKKNFAKS  301

Query: 1144  KWKKAVRVTTLMKRLR  1191
             KWK+A   T +++ +R
Sbjct: 302   KWKQAFNATAVVRHMR  317

>gi|406113|gb|AAA19670.1|  (L24907) protein kinase I [Rattus
             norvegicus]
            Length = 332

Score =  299 bits (758), Expect = 1e-79
 Identities = 146/316 (46%), Positives = 212/316 (66%), Gaps = 2/316 (0%)
 Frame = +1

Query: 250   YNQPSEVTDRYDLGQVIKTEEFCEIFRAKDKTTGKLHTCKKFQKRDGRKVRKAAKNEIGI  429
             + Q  ++ D YD   V+ T  F E+  A+DK T KL    K   K+       + +NEI +
Sbjct: 10    WKQAEDIRDIYDFRDVLGTGAFSEVILAEDKRTQKLVAIKCIAKKALEGKEGSMENEIAV  69

Query: 430   LKMVKHPNILQLVDVFVTRKEYFIFLELATGREVFDWILDQGYYSERDTSNVVRQVLEAV  609
             L  +KHPNI+ L D++ +      ++ ++L +G E+FD I+++G Y+ERD S ++ QVL+AV
Sbjct: 70    LHKIKHPNIVALDDIYESGGHLYLIMQLVSGGELFDRIVEKGGYTERDRSRLIFQVLDAV  129

Query: 610   AYLHSLKIVHRNLKLENLVYYNRLKNSKIVISDFHLAKLEN--GLIKEPCGTPEYLAPEV  783
             YLH L  IVHR+LK ENL+YY+   ++SKI+ISDF L+K+E+    ++    CGTP Y+APEV
Sbjct: 130   KYLHDLGIVHRDLKPENLLYYSLDEDSKIMISDFGLSKMEDPGSVLSTACGTPGYVAPEV  189
```

FIGURE 2L

```
Query:  784  VGRQRYGRPVDCWAIGVIMYILLSGNPPFYEEVEEDDYENHDKNLFRKILAGDYEFDSPY  963
             +  ++  Y +  VDCW+IGVI YILL G PPFY+E         +D  LF +IL  +YEFDSPY
Sbjct:  190  LAQKPYSKAVDCWSIGVIAYILLCGYPPFYDE--------NDAKLFEQILKAEYEFDSPY  241

Query:  964  WDDISQAAKDLVTRLMEVEQDQRITAEEAISHEWISGNAASDKNIKDGVCAQIEKNFARA  1143
             WDDIS +AKD +  LME + ++R T E+A+ H WI+G+ A DKNI    V  QI+KNFA++
Sbjct:  242  WDDISDSAKDFIRHLMEKDPEKRFTCEQALQHPWIAGDTALDKNIHQSVSEQIKKNFAKS  301

Query:  1144 KWKKAVRVTTLMKRLR  1191
             KWK+A    T +++ +R
Sbjct:  302  KWKQAFNRTAVVRHMR  317

>gi|9966875|ref|NP_065130.1| CamKI-like protein kinase [Homo sapiens]
  gb|AAG00534.1|AF286366_1 (AF286366) CamKI-like protein kinase [Homo sapiens]
          Length = 357

Score =  299 bits (757), Expect = 1e-79
 Identities = 142/332 (42%), Positives = 221/332 (65%), Gaps = 2/332 (0%)
 Frame = +1

Query:  256  QPSEVTDRYDLGQVIKTEEFCEIFRAKDKTTGKLHTCKKFQKRDGRKVRKAAKNEIGILK  435
             Q  ++    ++  + +  + T  F E+  A++K TGKL    K  K+ +      +  +NEI +L+
Sbjct:  15   QAEDIKKIFEFKETLGTGAFSEVVLAEEKATGKLFAVKCIPKKALKGKESSIENEIAVLR  74

Query:  436  MVKHPNILQLVDVFVTRKEYFIFLELATGREVFDWILDQGYYSERDTSNVVRQVLEAVAY  615
             +KH NI+ L D++ +     ++ ++L +G E+FD I+++G+Y+E+D  S ++RQVL+AV Y
Sbjct:  75   KIKHENIVALEDIYESPNHLYLVMQLVSGGELFDRIVEKGFYTEKDASTLIRQVLDAVYY  134

Query:  616  LHSLKIVHRNLKLENLVYYNRLKNSKIVISDFHLAKLE--NGLIKEPCGTPEYLAPEVVG  789
             LH + IVHR+LK ENL+YY++    + SKI+ISDF L+K+E       ++   CGTP Y+APEV+
Sbjct:  135  LHRMGIVHRDLKPENLLYYSQDEESKIMISDFGLSKMEGKGDVMSTACGTPGYVAPEVLA  194

Query:  790  RQRYGRPVDCWAIGVIMYILLSGNPPFYEEVEEDDYENHDKNLFRKILAGDYEFDSPYWD  969
             ++  Y +  VDCW+IGVI YILL G PPFY+E         +D  LF +IL  +YEFDSPYWD
Sbjct:  195  QKPYSKAVDCWSIGVIAYILLCGYPPFYDE--------NDSKLFEQILKAEYEFDSPYWD  246

Query:  970  DISQAAKDLVTRLMEVEQDQRITAEEAISHEWISGNAASDKNIKDGVCAQIEKNFARAKW  1149
             DIS +AKD +  LME + ++R T E+A  H WI+G+ A +KNI + V  AQI KNFA++KW
Sbjct:  247  DISDSAKDFIRNLMEKDPNKRYTCEQAARHPWIAGDTALNKNIHESVSAQIRKNFAKSKW  306

Query:  1150 KKAVRVTTLMKRLRAPEQSSTAAAQSASATDT  1245
              ++A    T +++ +R       S+  +  +AS + +
Sbjct:  307  RQAFNATAVVRHMRKLHLGSSLDSSNASVSSS  338

>gi|3893099|emb|CAA76937.1| (Y17917) calcium/calmodulin dependent
            protein kinase I [Drosophila melanogaster]
  gb|AAF59343.1| (AE003844) CaMKI gene product [alt 2] [Drosophila melanogaster]
          Length = 405

Score =  288 bits (729), Expect = 3e-76
 Identities = 152/388 (39%), Positives = 243/388 (62%), Gaps = 21/388 (5%)
 Frame = +1
```

FIGURE 2M

```
Query:  238  DKKNYNQPSEVTDRYDLGQVIKTEEFCEIFRAKDKTT-GKLHTCKKFQKRDGRKVRKAAK  414
             D K N+   + ++Y+L  ++ T  F E+  A+ K + G+     K  K+  +   ++  +
Sbjct:   17  DLKELNKQVSIEEKYNLHGLLGTGAFSEVRLAESKDSPGEHFAVKIIDKKALKGKEESLE  76

Query:  415  NEIGILKM---------------VKHPNILQLVDVFVTRKEYFIFLELATGREVFDWILD  549
             NEI +L+                 + HPNI+QL++  +   + ++  +EL TG E+FD I++
Sbjct:   77  NEIRVLRRFSANHFDGKCLNGTRLTHPNIVQLLETYEDKSKVYLVMELVTGGELFDRIVE  136

Query:  550  QGYYSERDTSNVVRQVLEAVAYLHSLKIVHRNLKLENLVYYNRLKNSKIVISDFHLAKLE  729
             +G Y+E+D S+++RQ+LEAV Y+H   +VHR+LK ENL+YY+     +SKI+ISDF L+K+E
Sbjct:  137  KGSYTEKDASHLIRQILEAVDYMHEQGVVHRDLKPENLLYYSPDDDSKIMISDFGLSKME  196

Query:  730  N-GLIKEPCGTPEYLAPEVVGRQRYGRPVDCWAIGVIMYILLSGNPPFYEEVEEDDYENH  906
             +  G++     CGTP Y+APEV+ ++ YG+ VD W+IGVI YILL G PPFY+E            +
Sbjct:  197  DSGIMATACGTPGYVAPEVLAQKPYGKAVDVWSIGVISYILLCGYPPFYDE--------N  248

Query:  907  DKNLFRKILAGDYEFDSPYWDDISQAAKDLVTRLMEVEQDQRITAEEAISHEWISGNAAS  1086
             D NLF +IL GD+EFDSPYWD+IS++AK  +   LM V  ++R T  ++A+ H WISGN AS
Sbjct:  249  DANLFAQILKGDFEFDSPYWDEISESAKHFIKNLMCVTVEKRYTCKQALGHAWISGNEAS  308

Query: 1087  DKNIKDGVCAQIEKNFARAKWKKAVRVTTLMKRLRAPEQSSTAAA----QSASATDTATP  1254
             +NI    V Q++KNFA++WK+A   T+++++      +S + A        ++S  D+ TP
Sbjct:  309  SRNIHGTVSEQLKKNFAKSRWKQAYYAATVIRQMQRMALNSNSNANFDSSNSSNQDSTTP  368

Query: 1255  GAAGGATAAAASGATSAPEGDAARAAKS  1338
              AA GA  +    +  ++ A        KS
Sbjct:  369  TAATGAWTSNVLSSQQSVQSHAQEMNKS  396

>gi|4007153|emb|CAA19296.1| (AL023754) dJ272L16.1 (Rat Ca2+/Calmodulin
            dependent Protein Kinase LIKE protein) [Homo sapiens]
            Length = 460

Score =  286 bits (724), Expect = 1e-75
 Identities = 157/408 (38%), Positives = 233/408 (56%), Gaps = 5/408 (1%)
 Frame = +1

Query:  256  QPSEVTDRYDLGQVIKTEEFCEIFRAKDKTTGKLHTCKKFQKRDGRKVRKAAKNEIGILK  435
             Q + +     +V+ +   F E+F  K + TGKL    K  +K      +   + +NEI +LK
Sbjct:   15  QTTNIRKTFIFMEVLGSGAFSEVFLVKQRLTGKLFALKCIKKSPAFR-DSSLENEIAVLK  73

Query:  436  MVKHPNILQLVDVFVTRKEYFIFLELATGREVFDWILDQGYYSERDTSNVVRQVLEAVAY  615
             +KH NI+ L D++   +    Y++ ++L +G E+FD  IL++G Y+E+D S V++QVL AV Y
Sbjct:   74  KIKHENIVTLEDIYESTTHYYLVMQLVSGGELFDRILERGVYTEKDASLVIQQVLSAVKY  133

Query:  616  LHSLKIVHRNLKLENLVYYNRLKNSKIVISDFHLAKLE-NGLIKEPCGTPEYLAPEVVGR  792
             LH   IVHR+LK ENL+Y      +NSKI+I+DF L+K+E NG++      CGTP Y+APEV+ +
Sbjct:  134  LHENGIVHRDLKPENLLYLTPEENSKIMITDFGLSKMEQNGIMSTACGTPGYVAPEVLAQ  193

Query:  793  QRYGRPVDCWAIGVIMYILLSGNPPFYEEVEEDDYENHDKNLFRKILAGDYEFDSPYWDD  972
             + Y + VDCW+IGVI YILL G PPFYEE E                     LF KI  G YEF+SP+WDD
Sbjct:  194  KPYSKAVDCWSIGVITYILLCGYPPFYEETE--------SKLFEKIKEGYYEFESPFWDD  245

Query:  973  ISQAAKDLVTRLMEVEQDQRITAEEAISHEWISGNAASDKNIKDGVCAQIEKNFARAKWK  1152
             IS++AKD + L+E +++R T E+A+SH WI GN A   ++I   V QI+KNFA++KW+
Sbjct:  246  ISESAKDFICHLLEKDPNERYTCEKALSHPWIDGNTALHRDIYPSVSLQIQKNFAKSKWR  305
```

FIGURE 2N

```
Query: 1153 KAVRVTTLMKRLRAPEQS--STAAAQSASATDTATPGAAGGATAAAASGATSAPEGDAAR 1326
              +A    ++ +R   + S           T +      ++       T AP  D +
Sbjct:  306 QAFNAAAVVHHMRKLHMNLHSPGVRPEVENRPPETQASETSRPSSPEITITEAPVLDHSV 365

Query: 1327 AAKSDNVAPADRSATPATDG--SATPATDGSVTPATDGSITPATDGSV 1464
              A +   P       P G S    +GS+        S+ P   GS+
Sbjct:  366 ALPALTQLPCQHGRRPTAPGGRSLNCLVNGSL--HISSSLVPMHQGSL 411

>gi|4678722|emb|CAB41259.1| (AL049688) hypothetical protein [Homo
            sapiens]
         Length = 481

Score =  286 bits (724), Expect = 1e-75
 Identities = 157/408 (38%), Positives = 233/408 (56%), Gaps = 5/408 (1%)
 Frame = +1

Query:  256 QPSEVTDRYDLGQVIKTEEFCEIFRAKDKTTGKLHTCKKFQKRDGRKVRKAAKNEIGILK 435
            Q + +       +V+ +     F E+F  K + TGKL     K   +K   +   +NEI +LK
Sbjct:   20 QTTNIRKTFIFMEVLGSGAFSEVFLVKQRLTGKLFALKCIKKSPAFR-DSSLENEIAVLK 78

Query:  436 MVKHPNILQLVDVFVTRKEYFIFLELATGREVFDWILDQGYYSERDTSNVVRQVLEAVAY 615
             +KH NI+ L D++ +    Y++ ++L +G E+FD  IL++G  Y+E+D S  V++QVL AV Y
Sbjct:   79 KIKHENIVTLEDIYESTTHYYLVMQLVSGGELFDRILERGVYTEKDASLVIQQVLSAVKY 138

Query:  616 LHSLKIVHRNLKLENLVYYNRLKNSKIVISDFHLAKLE-NGLIKEPCGTPEYLAPEVVGR 792
            LH   IVHR+LK ENL+Y   +NSKI+I+DF L+K+E NG++    CGTP Y+APEV+ +
Sbjct:  139 LHENGIVHRDLKPENLLYLTPEENSKIMITDFGLSKMEQNGIMSTACGTPGYVAPEVLAQ 198

Query:  793 QRYGRPVDCWAIGVIMYILLSGNPPFYEEVEEDDYENHDKNLFRKILAGDYEFDSPYWDD 972
            + Y + VDCW+IGVI YILL G PPFYEE E            LF KI  G YEF+SP+WDD
Sbjct:  199 KPYSKAVDCWSIGVITYILLCGYPPFYEETE---------SKLFEKIKEGYYEFESPFWDD 250

Query:  973 ISQAAKDLVTRLMEVEQDQRITAEEAISHEWISGNAASDKNIKDGVCAQIEKNFARAKWK 1152
            IS++AKD +   L+E +   ++R T E+A+SH WI GN A    ++I   V  QI+KNFA++KW+
Sbjct:  251 ISESAKDFICHLLEKDPNERYTCEKALSHPWIDGNTALHRDIYPSVSLQIQKNFAKSKWR 310

Query: 1153 KAVRVTTLMKRLRAPEQS--STAAAQSASATDTATPGAAGGATAAAASGATSAPEGDAAR 1326
              +A    ++ +R   + S           T +      ++       T AP  D +
Sbjct:  311 QAFNAAAVVHHMRKLHMNLHSPGVRPEVENRPPETQASETSRPSSPEITITEAPVLDHSV 370

Query: 1327 AAKSDNVAPADRSATPATDG--SATPATDGSVTPATDGSITPATDGSV 1464
              A +   P       P G S    +GS+        S+ P   GS+
Sbjct:  371 ALPALTQLPCQHGRRPTAPGGRSLNCLVNGSL--HISSSLVPMHQGSL 416

Hmmer search results (Pfam):
Model    Description                         Score    E-value   N
PF00069  Eukaryotic protein kinase domain    229.1    6.5e-65   1
CE00022  CE00022 MAGUK_subfamily_d           105.3    5.5e-31   2
CE00287  CE00287 PTK_Eph_orphan_receptor     -71.4    0.0011    1
CE00292  CE00292 PTK_membrane_span           -87.6    0.00079   1
CE00291  CE00291 PTK_fgf_receptor            -125.1   0.13      1
CE00286  E00286 PTK_EGF_receptor             -159.5   0.3       1
CE00290  CE00290 PTK_Trk_family              -188.3   0.028     1
CE00016  CE00016 GSK_glycogen_synthase_kinase -237.5  0.0016    1
```

FIGURE 20

Parsed for domains:

| Model | Domain | seq-f | seq-t | hmm-f | hmm-t | score | E-value |
|---|---|---|---|---|---|---|---|
| CE00022 | 1/2 | 117 | 152 .. | 118 | 153 .. | 4.3 | 0.35 |
| CE00286 | 1/1 | 43 | 245 .. | 1 | 263 [] | -159.5 | 0.3 |
| CE00292 | 1/1 | 26 | 259 .. | 1 | 288 [] | -87.6 | 0.00079 |
| CE00290 | 1/1 | 29 | 266 .. | 1 | 282 [] | -188.3 | 0.028 |
| CE00291 | 1/1 | 24 | 266 .. | 1 | 285 [] | -125.1 | 0.13 |
| CE00287 | 1/1 | 24 | 284 .. | 1 | 260 [] | -71.4 | 0.0011 |
| PF00069 | 1/1 | 37 | 286 .. | 14 | 278 .] | 229.1 | 6.5e-65 |
| CE00022 | 2/2 | 182 | 286 .. | 188 | 283 .. | 100.8 | 1.2e-29 |
| CE00016 | 1/1 | 3 | 357 .. | 1 | 433 [] | -237.5 | 0.0016 |

FIGURE 2P

```
   1 AATGAAATCC TGTATCTACA AAAAAATTTT TAAAAATTAG CCAGTTGTGG
  51 TGGTGTGCAC CTATGGTCCA GTCCTAGCTA CTCAGGAGGC TGAGGTGGGA
 101 GGATCGCTTG AGCCCAGGAG GTTGAGGCTG GAATGAGCTG TGATCATTCC
 151 ACTGCATTCC AGCCTGGGTG CCACTGCATT CCAGCCTGGG TGACAGAACA
 201 GCTGGGCATG GTGCGGGTGC CTGTAATCCC AGCTGCGGTG GGAGGATCGT
 251 TTGAGTTCAG GAGCTCTGGG CTGCAGTGCG CTATGCCAGT TGGGTGTCTA
 301 CACTAAGTTT GGCATTAGTA TGGTGACTTC CTGGGAGCTA GAGCTCATCA
 351 GGTTGCCTAA AGGAGGGGTG AAGCAACCAA GGTCAGAGAC GAAGCAGGTC
 401 AAAACTCCTG TGCTGATCAG TAGTGGGCTT GTGCCCATGA ATAGCCACTG
 451 CACTCCAGCC TGGGCAACAT AGTGAGACTT GTCTCTAAAA AAAGAAAGAA
 501 AGAAAGAAAA GAAAAGAAAA GAAATAGGTC TTCCAGAATC CCCCCCATGT
 551 GTCCTGAATC AATCATAACC CCTCCTTTTC TCTTAGAAGG GACCATTATC
 601 TGACTCTGCT TATTTCCTAG CTTTTCTTTA TAGCTCTACT GCTGTGTTTG
 651 TATCCCCCTT ACGGGTTTGT TCTGCCTGTT TGAACTCTAT CAATAGACTC
 701 ATACTATATG TATTCTTTTG TGTCTTTTTG CACTTAACAC TGTGTAAGAG
 751 TCACCAGGTG GTTGGGTATA GCTGTAGCTC CTTTGTTTCC ATTGCTATAT
 801 AATATTCCAT TGTGTGACTC TACCACAATA CATCCTGTTG GTGGTGGTAT
 851 TTGGTCTGTT TTCAATTTTT GGCGATTATG TATATGGCTA CTATGAGCAT
 901 TGTATGACTG TCCTGATGCA CGAATATGTG CACTTCTGTA GGCACGTATT
 951 TAGGAGTGCA ATTGCTGGTT CATAGGGTAT GTTTGTTTGA CTTTAGTGGT
1001 TTTACCAAAC TGCTTTACAA AGGGGAGTTT GCCCTCTCCT AGCAGTGCTC
1051 ACGTTCTTCA TATATCCACT AACACTTGTT AGCTCTAGAC CTTCAGAGAT
1101 GACTAGCAGG TGGGTGGGTG GTTATAGCCC CCTTCATCTG TAAAATAGCT
1151 GAAATTTAAA TAAACTGTTT GATAAGCCTT TTTTTGAATG TATAGAATAC
1201 AAAACTATTC CCTTATATAT CAGCTTAATA CATTTTTTCA TATGTAGGCT
1251 GTTGCACTTC AGGCAGCCAA GCTGAGTAGC TGGATGTCTA GCCAGAAAAG
1301 CAGGGGTAGG ATCTAAGCCT GCCTATCCTC TAGCCCCTCC TGGTATGGTC
1351 TCTGCCCCTA GCTTGGCCTG AGCCAGGTTG GGGTCTCCCA AAAGCAGCCC
1401 CTATGTTGTG GGGAAGTGGA GAGTAGTACA GCTAAGCCAG ACCCCATTGT
1451 GCCCGCAGGT TAGAGCCTGG CAATGCCGTT TGGGTGTGTG ACTCTGGGCG
1501 ACAAGAAGAA CTATAACCAG CCATCGGAGG TGACTGACAG ATATGATTTG
1551 GGACAGGTCA TCAAGACGTG AGTGCCGGGC CTGTCAGGCA GGCTGGGTG
1601 GGCTGGTGAG CAGGGGCTAG GGAAGTGGCA GTGGAGTGCA GCTGATGCTA
1651 AGGCCAGGCC TGAGTGGGTG CCTGTCGGCT GCAGTGAGGA GTTTTGTGAA
1701 ATCTTCCGGG CCAAGGACAA GACGACAGGC AAGCTGCACA CCTGCAAGAA
1751 GTTCCAGAAG CGGGACGGCC GCAAGGTGCG GAAAGCTGCC AAGAACGAGA
1801 TAGGCATCCT CAAGATGTGA GTTTGAGGCC TGGGATTGGG GCGGGGTGGG
1851 AGGCAGCAGG GAAGGGCTTA GAGGGCAAGT GGCCTCAGGC AGTCCCAGCC
1901 TCTGCCAAT TAGTACTGCT GTGGCCACTG TGGTGACCAC AGCCTCTCCC
1951 AGGGGTTCAT CCAGCCCTAA CTACTGGCTC CCCTCCCTGT CGCCAGGGTG
2001 AAGCATCCCA ACATCCTACA GCTGGTGGAT GTGTTTGTGA CCCGCAAGGA
2051 GTACTTTATC TTCCTGGAGC TGTGAGTGTG GGTCTGGGGA CCCAAGATTC
2101 CCCAGCGCCC AGGGCTTTCA CCTGTCCCAC CCTCTGCAGC TAAGGAAACC
2151 CCCTTTCTGG ACCCTTGGCG TCCCAGGTCC CTGTGCCTTG CTCAGCCAGC
2201 TGCCTGGCGT AGGCAGCTCA CCCAAGTGCT CCTGCCCTAC CCCTGATTCT
2251 GCCCACGCCA GGCTCAGGGG CTGGTGTCCC TCAGGGCCAC GGGGAGGGAG
2301 GTGTTTGACT GGATCCTGGA CCAGGGCTAC TACTCGGAGC GAGACACAAG
2351 CAACGTGGTA CGGCAAGTCC TGGAGGCCGT GGCCTATTTG CACTCACTCA
2401 AGATCGTGCA CAGGAATCTC AAGGTGAGGG CAGAGCCAGA GTCAAAGGGC
2451 CAGTTGGCAG CTGGGCTGGT GCTGGGGTGG GCAGCACCTC AGGGCCTTGG
2501 TCTAGCCTCC AAGGTCCTCA TGGTGTCTTC TGCTCACCCA CATGCTATTC
2551 TCACACCACA GCTGGAGAAC CTGGTTTACT ACAACCGGCT GAAGAACTCG
2601 AAGATTGTCA TCAGTGACTT CCATCTGGCT AAGCTAGAAA ATGGCCTCAT
2651 CAAGGAGCCC TGTGGGACCC CCGAGTATCT GGGCAAGCAG GGGGTGGGGC
2701 AGGGGCAGGG GGATAATGGG GGGCAGCCTT CAGGGAGCTG CTCTGGGCAG
2751 GGGGAAAATG TGCTCATCTC AGGAAGCTGG TGTGGATGGT ACTGGACCTG
2801 GCTAGGCCTG ATACTGACCA GCAGATGGGC GCTGTGTTTG TAGCCCCAGA
2851 GGTGGTAGGC CGGCAGCGGT ATGGACGCCC TGTGGACTGC TGGGCCATTG
2901 GAGTCATCAT GTACATCCTG TGAGTGGACA GATGGACAAG CAGGCTTGCA
```

FIGURE 3A

```
2951 GTCAGATGGG GTGGGGGCAT GTGTCTGTGG CCTTTCTGTG TGACCCTTCC
3001 CCCATGCAGG CTTTCAGGCA ACCCACCTTT CTATGAGGAG GTGGAAGAAG
3051 ATGATTATGA GAACCATGAT AAGAATCTCT TCCGCAAGAT CCTGGCTGGT
3101 GACTATGAGT TTGACTCTCC ATATTGGGAT GATATTTCGC AGGCAGGTGA
3151 GGAGGTGCCT GCCCAGCACT TGGTAGAACG CAAGGGAGTG GGGAGGGTGT
3201 CCTGCTCTCA TCTTCCTCTG TGGTATTCTG CTTCTGTCCC CCAGCCCATT
3251 TATCACCTCT AGACATTGAG ATGGGGTGCC CATGACTATC CCCTCCTTGG
3301 TTTTGTCCAC AGCCAAAGAC CTGGTCACAA GGCTGATGGA GGTGGAGCAA
3351 GACCAGCGGA TCACTGCAGA AGAGGCCATC TCCCATGAGT GGTGAGCAGG
3401 GTCCAGGGGA GGGTGGGAGA GGCCAGGGTC CCCCTCACAC CCAGCAGCCC
3451 CATCTTTGAG GCCTAGAAGG GGTGCAGGTA CCTAGAGCTC AGGGCAGCCC
3501 AGAGGCTCTG CCTGGTAGTC CCTGGATGCC ACATAGAAGG GCTGAGCAGA
3551 GTCTCCACAA AGGCTCATTC TCTCAGATCC AGACACACTT GCACCCTTTC
3601 CAGGATTTCT GGCAATGCTG CTTCTGATAA GAACATCAAG GATGGTGTCT
3651 GTGCCCAGAT TGAAAAGAAC TTTGCCAGGG CCAAGTGGAA GGTAAGGCTT
3701 GGATAACTCC CTTCTTGGCT CTATCCCAAG TATTGCTTCT GGCACTCAGT
3751 TTCTTGCCTG CATCACACCC CTGCAGCCAC ACACAAGCTT TTCTCAGGCC
3801 ATCAGGTGTG GGTGTAGCCA CTGTGATTAC CTTAAGTAGG AGTGCTGAGC
3851 AGCTGAGTAC TTGGCCCTGG GGTGGATGGA GGTGGCCGGG GGTACTATGG
3901 AAGGAGTTTG GTTTGGTCAC TGCCAAGCAA TGGATCCAGC AAGCCTCACC
3951 CTTAGCCTTT CTCCACTGTG CTCCTTTCAG AAGGCTGTCC GAGTGACCAC
4001 CCTCATGAAA CGGCTCCGGG CACCAGAGCA GTCCAGCACG GCTGCAGCCC
4051 AGTCGGCCTC AGCCACAGAC ACTGCCACCC CCGGGGCTGC AGGTGGGGCC
4101 ACAGCTGCAG CTGCGAGTGG AGCTACCTCA GCCCCTGAGG GTGATGCTGC
4151 TCGTGCTGCA AAGAGTGATA ATGTGGCCCC CGCAGACCGT AGTGCCACCC
4201 CAGCCACAGA TGGAAGTGCC ACCCCAGCCA CTGATGGCAG TGTCACCCCA
4251 GCCACCGATG GAAGCATCAC TCCAGCCACT GATGGGAGTG TCACCCCAGC
4301 CACTGACAGG AGCGCTACTC CAGCCACTGA TGGGAGAGCC ACACCAGCCA
4351 CAGAAGAGAG CACTGTGCCC ACCACCCAAA GCAGTGCCAT GCTGGCCACC
4401 AAGGCAGCTG CCACCCCTGA GCCGGCTATG GCCCAGCCGG ACAGCACAGC
4451 CCCAGAGGGC GCCACAGGCC AGGCTCCACC CTCTAGTAAA GGGGAAGAGG
4501 CTGCTGGTTA TGCCCAGGAG TCTCAAAGGG AGGAGGCCAG CTGAGTAGGC
4551 AGCCTGGTGA GGGGGGGCAG GGGATGGGCA GGAGGGTGGG AGAGTGGATG
4601 AGGGGCTTCT CACTGTACAT AGAGTCACTG GCATGATGCC CTCGCTCCCC
4651 CATGCCCCCA CATCCCAGTG GGGCATAACT AGGGGTCACG GGAGAGCAGT
4701 CTCGTCTCCT GTGTGTATGT GTGTGAGTGG TGGGCAGGCC AGTGGCAGGG
4751 CCGGCCCCAG CCCCTGCATG GATTCCTTGT GGCTTTTCTG TCTTTTGCTA
4801 GCTTCACCAG TTTCTGTTCC TTGTGGGATG CTGCTCTAGG GATACTCAGG
4851 GGGCTCCTGC TCTCCTTTCC CTTCCCTTCT TGCCTCACCA TTCCCCTAGG
4901 CAGGCCCTGC AGGTCCCACA CTCTCCCAGG CCCTAAACTT GGGCGGCCTT
4951 GCCCTGAGAG CTGGTCCTCC AGCGAGGCCC TGTCAGCGGT CTTAGGCTCC
5001 TGCACATGAA GGTGTGTGCC TGTGGTGTGT GGGCTGCTCT AGGAGCAGAT
5051 ACAGGCTGGT ATAGAGGATG CAGAAAGGTA GGGCAGTATG TTTAAGTCCA
5101 GACTTGGCAC ATGGCTAGGG ATACTGCTCA CTAGCTGTGG AGGTCCTCAG
5151 GAGTGGAGAG AATGAGTAGG AGGGCAGAAG CTTCCATTTT TGTCCTTCCT
5201 AAGACCCTGT TATTTGTGTT ATTTCCTGCC TTTCCGAGTC CTGCAGTGGG
5251 CTGCCCTGTA CCCTGAACCT CATGAGCCTC TAAGGGAAAG GAGGAACAAT
5301 TAGGACGTGG CAATGAGACC TGGCAGGGCA GAGTACAAGC CCAGCACCCA
5351 GTGTCCCAGC CTTAATGGGT CCTTACCATG GGCCAAACAG GGAGGGCTGA
5401 TACCTCCTTG CTCTTCCTAG ATGCCCACCT CCTACAATCT CAGCCCACAA
5451 GTCCTCTCCA CCTAGGGGGC TTGCTGCATG GCAATAACTC ATAATTTGAT
5501 TTGGAGGTTT GCCCTTTACA GGGGCAGATT TTCTGCTCAG TTCAACAATG
5551 AAATGAAGAG GAACTCCCTC TTTCTACAGC TCACTTCTAT CAGAGGCCCA
5601 GGTGCCTCAG AGCCACATTG AGTTGCTTTT TCTGGGATGA GGAAGTAGGG
5651 TTAAACTCCC CAGTTTCCTG AGGGAGGCTC CTGACAGGTG CCCTTTGTCA
5701 GACCCTACCA CAGCCTGGAT AGGCAGCCAC ATTGGTCCTC GCCCTTGCTC
5751 GGCACTCCGT GGTGGTCCTG CCCTTCTCCC TGCATGCCTG TGGGTCTGCT
5801 CTGGTGTGTG AAGGTCGGTG GGTTAACTGT GTGCCTACTG AACCTGGCAA
5851 ATAAACATCA CCCTGCAAAG CCTCTGGCCA CCCTCTCGCC TTTGCTTCCT
```

FIGURE 3B

```
5901 CTGTCCTACT GGGGAGGAGC CCCTGGAAGG CAGTGGGGAA GGGAGAGGCT
5951 GGGAGCAGGT TCACAAGTAG TGGCTGGGAG TAGTAGTGAA CAGTGCCCTG
6001 TGGATTTCTT GGGCTGAGGG TGAAGATCAT CCTCACCACA GTGTATTCCT
6051 CAATGGTGGT GGTGGTGGGG GTCCTCTGAA CTCTAGAAAT CCATGTGAGT
6101 AGTGGGTCTT GGGCTGCATT TGGACCAAGG AATACTCCCT GGGCTGAGAG
6151 CTCAAGTAAG GGCTGCTGTT TTTGACTCCT GTTGACCGAG GAGCCTTACT
6201 CTTGATTTAG GCATAGAGCT GGAATCTACC TGGGCCAGCC AGCGCAAGGA
6251 CAGACCCTGC TCATAGCCAA AGATAGCTTC CCTGAGCTAG GGAGAGGGTG
6301 TAGGGTGAGC AATGCACAAA GATTCTATGC TGCTCTGTGT TGATTCCTTC
6351 TTTCTGTGAA CACCTGTGCT TTCCACCTAT GCCCCAAATG AAATCTCACT
6401 CTGGGTCTAT TTCAGCTGGA GCAGATCAGC TTTATATTAT GGGACTATGC
6451 ACAGGGTTTC TTCTGGGTAG AGGGAGTAAC ACTGCCACAG ATACTAAGCC
6501 TAAAAACCCA AAAGTTGACT TACTCCAGCC CAGGTGGGCC TGGGTGAACT
6551 CACCAGGGAT GCTGCTCTCT GGGAGGACCT CAAAGATAAC CTCCTCAAGG
6601 ATAACTTCTC TGATGTGGGA ATAATAAAAA GGATTTGTTA GTCTCTAGTC
6651 TTTGAAGCAT CTGGGCCTCC AAAATTCCAA CCCTACTACA GTCTCAAGCA
6701 TAACTGATCC TCCTGAGAGC TAAGAGCTAA AGTCAGGGTA CTGGCCCTAG
6751 TGTCTCCAAA CTCAAGGATA GTCATATCTT ACTTGGATGA AGCCAAGGTT
6801 GGCCTGGGGT GACCTGAGGG ACTGGGGCCT ATGTGTCCAT CTTTCTAGAA
6851 TCGCCCGGAA CTGAGGACTG AGAGGGTAGG GTATTGTGGT CTATGGGAAC
6901 TACAGACCAT AGCGCATGGT CCATCACTGT CCAGAGCCCA AGGGACCCAT
6951 CGGGACCATT GTTCTATTCC CTTGCGGCTG CGGTTTTCTC TGCCTTGGCC
7001 CAGCCTGCCT CGCGCCAGCT CTGGCATGGG ACCACAATGC GCTGCCTTGC
7051 CCTGGAAAAG GGTCCAGCTG GCAGCCTCGC TGCTCCCCGC CTTGATATAA
7101 TGCTGCGCTC TCAAGTGGCA GGTCGAGTCT CCCCAGAGGA CGCCTGAGAG
7151 CGACCGCGCT CCGCCCAGGA TTCTCTACGG CCTCGGGGCC GCTAAGCCCC
7201 GCCCATAGTT CCGCCCATCC GAGAATTTGT CCAATCCAGG CGAAGTATTC
7251 ACGCTCCGCC CAAAGTTTTG TGTTGTCACT TCCGGCCCGC TCCAGGAAGT
7301 CGTGCTGCGG AGCCAAATTT GAAGCAAGCG GAGGCGCGGG GGCGCGTCTA
7351 CGAAGCCGGA CCTGTAGCAG TTTCTTTGGC TGCCTGGGCC CCTTGAGTCC
7401 AGCCATCATG CCTATCCGTG CTCTGTGCAC TATCTGCTCC GACTTCTTCG
7451 ATCACTCCCG CGACGTGGCC GCCATCCACT GCGGCCACAC CTTCCACTTG
7501 CAGTGGTGAG TGACTGCAGT GTTGGGGCCC GGTGTTTGCC CG
```

FEATURES:
Start:   1473
Exon:    1473-1567
Intron:  1568-1684
Exon:    1685-1816
Intron:  1817-1996
Exon:    1997-2071
Intron:  2072-2284
Exon:    2285-2423
Intron:  2424-2561
Exon:    2562-2682
Intron:  2683-2843
Exon:    2844-2919
Intron:  2920-3009
Exon:    3010-3146
Intron:  3147-3312
Exon:    3313-3391
Intron:  3392-3603
Exon:    3604-3691
Intron:  3692-3980
Exon:    3981-4541
Stop:    4542

FIGURE 3C

CHROMOSOME MAP POSITION:
Bac Accession #: AC068701
Chromosome: 3

ALLELIC VARIANTS (SNPs):

| DNA Position | Major | Minor | Domain | Protein Position | Major | Minor |
|---|---|---|---|---|---|---|
| 234 | T | A | Beyond ORF(5') | | | |
| 328 | T | C | Beyond ORF(5') | | | |
| 1499 | C | T | Exon | 9 | G | G |
| 3022 | T | C | Exon | 217 | N | N |
| 3295 | C | T | Intron | | | |
| 4677 | T | A | Beyond ORF(3') | | | |
| 5583 | C | T A | Beyond ORF(3') | | | |
| 6242 | G | C | Beyond ORF(3') | | | |
| 7264 | G | A | Beyond ORF(3') | | | |

Context:

| DNA Position | |
|---|---|
| 234 | AATGAAATCCTGTATCTACAAAAAAATTTTTAAAAATTAGCCAGTTGTGGTGGTGTGCAC CTATGGTCCAGTCCTAGCTACTCAGGAGGCTGAGGTGGGAGGATCGCTTGAGCCCAGGAG GTTGAGGCTGGAATGAGCTGTGATCATTCCACTGCATTCCAGCCTGGGTGCCACTGCATT CCAGCCTGGGTGACAGAACAGCTGGGCATGGTGCGGGTGCCTGTAATCCCAGC [T,A] GCGGTGGGAGGATCGTTTGAGTTCAGGAGCTCTGGGCTGCAGTGCGCTATGCCAGTTGGG TGTCTACACTAAGTTTGGCATTAGTATGGTGACTTCCTGGGAGCTAGAGCTCATCAGGTT GCCTAAAGGAGGGGTGAAGCAACCAAGGTCAGAGACGAAGCAGGTCAAAACTCCTGTGCT GATCAGTAGTGGGCTTGTGCCCATGAATAGCCACTGCACTCCAGCCTGGGCAACATAGTG AGACTTGTCTCTAAAAAAAGAAAGAAAGAAAGAAAAGAAAAGAAATAGGTCTTCC |
| 328 | TTTTAAAAATTAGCCAGTTGTGGTGGTGTGCACCTATGGTCCAGTCCTAGCTACTCAGGA GGCTGAGGTGGGAGGATCGCTTGAGCCCAGGAGGTTGAGGCTGGAATGAGCTGTGATCAT TCCACTGCATTCCAGCCTGGGTGCCACTGCATTCCAGCCTGGGTGACAGAACAGCTGGGC ATGGTGCGGGTGCCTGTAATCCCAGCTGCGGTGGGAGGATCGTTTGAGTTCAGGAGCTCT GGGCTGCAGTGCGCTATGCCAGTTGGGTGTCTACACTAAGTTTGGCATTAGTATGGTGAC [T,C] TCCTGGGAGCTAGAGCTCATCAGGTTGCCTAAAGGAGGGGTGAAGCAACCAAGGTCAGAG ACGAAGCAGGTCAAAACTCCTGTGCTGATCAGTAGTGGGCTTGTGCCCATGAATAGCCAC TGCACTCCAGCCTGGGCAACATAGTGAGACTTGTCTCTAAAAAAAGAAAGAAAGAAAGAA AAGAAAAGAAAAGAAATAGGTCTTCCAGAATCCCCCCCATGTGTCCTGAATCAATCATAA CCCCTCCTTTTCTCTTAGAAGGGACCATTATCTGACTCTGCTTATTTCCTAGCTTTTCTT |
| 1499 | ACAAAACTATTCCCTTATATATCAGCTTAATACATTTTTTTCATATGTAGGCTGTTGCACT TCAGGCAGCCAAGCTGAGTAGCTGGATGTCTAGCCAGAAAAGCAGGGGTAGGATCTAAGC CTGCCTATCCTCTAGCCCCTCCTGGTATGGTCTCTGCCCCTAGCTTGGCCTGAGCCAGGT TGGGGTCTCCCAAAAGCAGCCCCTATGTTGTGGGGAAGTGGAGAGTAGTACAGCTAAGCC AGACCCCATTGTGCCCGCAGGTTAGAGCCTGGCAATGCCGTTTGGGTGTGTGACTCTGGG [C,T] GACAAGAAGAACTATAACCAGCCATCGGAGGTGACTGACAGATATGATTTGGGACAGGTC ATCAAGACGTGAGTGCCGGGCCTGTCAGGCAAGGCTGGGTGGGCTGGTGAGCAGGGGCTA GGGAAGTGGCAGTGGAGTGCAGCTGATGCTAAGGCCAGGCCTGAGTGGGTGCCTGTCGGC TGCAGTGAGGAGTTTTGTGAAATCTTCCGGGCCAAGGACAAGACGACAGGCAAGCTGCAC ACCTGCAAGAAGTTCCAGAAGCGGGACGGCCGCAAGGTGCGGAAAGCTGCCAAGAACGAG |
| 3022 | GGCAGCCTTCAGGGAGCTGCTCTGGGCAGGGGGAAAATGTGCTCATCTCAGGAAGCTGGT |

FIGURE 3D

```
         GTGGATGGTACTGGACCTGGCTAGGCCTGATACTGACCAGCAGATGGGCGCTGTGTTTGT
         AGCCCCAGAGGTGGTAGGCCGGCAGCGGTATGGACGCCCTGTGGACTGCTGGGCCATTGG
         AGTCATCATGTACATCCTGTGAGTGGACAGATGGACAAGCAGGCTTGCAGTCAGATGGGG
         TGGGGGCATGTGTCTGTGGCCTTTCTGTGTGACCCTTCCCCCATGCAGGCTTTTCAGGCAA
         [T,C]
         CCACCTTTCTATGAGGAGGTGGAAGAAGATGATTATGAGAACCATGATAAGAATCTCTTC
         CGCAAGATCCTGGCTGGTGACTATGAGTTTGACTCTCCATATTGGGATGATATTTCGCAG
         GCAGGTGAGGAGGTGCCTGCCCAGCACTTGGTAGAACGCAAGGGAGTGGGGAGGGTGTCC
         TGCTCTCATCTTCCTCTGTGGTATTCTGCTTCTGTCCCCCAGCCCATTTATCACCTCTAG
         ACATTGAGATGGGGTGCCCATGACTATCCCCTCCTTGGTTTTGTCCACAGCCAAAGACCT

3295     CCTTCCCCCATGCAGGCTTTCAGGCAACCCACCTTTCTATGAGGAGGTGGAAGAAGATGA
         TTATGAGAACCATGATAAGAATCTCTTCCGCAAGATCCTGGCTGGTGACTATGAGTTTGA
         CTCTCCATATTGGGATGATATTTCGCAGGCAGGTGAGGAGGTGCCTGCCCAGCACTTGGT
         AGAACGCAAGGGAGTGGGGAGGGTGTCCTGCTCTCATCTTCCTCTGTGGTATTCTGCTTC
         TGTCCCCCAGCCCATTTATCACCTCTAGACATTGAGATGGGGTGCCCATGACTATCCCCT
         [C,T]
         CTTGGTTTTGTCCACAGCCAAAGACCTGGTCACAAGGCTGATGGAGGTGGAGCAAGACCA
         GCGGATCACTGCAGAAGAGGCCATCTCCCATGAGTGGTGAGCAGGGTCCAGGGGAGGGTG
         GGAGAGGCCAGGGTCCCCCTCACACCCAGCAGCCCCATCTTTGAGGCCTAGAAGGGGTGC
         AGGTACCTAGAGCTCAGGGCAGCCCAGAGGCTCTGCCTGGTAGTCCCTGGATGCCACATA
         GAAGGGCTGAGCAGAGTCTCCACAAAGGCTCATTCTCTCAGATCCAGACACACTTGCACC

4677     CAAAGCAGTGCCATGCTGGCCACCAAGGCAGCTGCCACCCCTGAGCCGGCTATGGCCCAG
         CCGGACAGCACAGCCCCAGAGGGCGCCACAGGCCAGGCTCCACCCTCTAGTAAAGGGGAA
         GAGGCTGCTGGTTATGCCCAGGAGTCTCAAAGGGAGGAGGCCAGCTGAGTAGGCAGCCTG
         GTGAGGGGGGGCAGGGATGGGCAGGAGGGTGGGAGAGTGGATGAGGGGCTTCTCACTGT
         ACATAGAGTCACTGGCATGATGCCCTCGCTCCCCCATGCCCCCACATCCCAGTGGGGCAT
         [T,A]
         ACTAGGGGTCACGGGAGAGCAGTCTCGTCTCCTGTGTGTATGTGTGTGAGTGGTGGGCAG
         GCCAGTGGCAGGGCCGGCCCCAGCCCCTGCATGGATTCCTTGTGGCTTTTCTGTCTTTTG
         CTAGCTTCACCAGTTTCTGTTCCTTGTGGGATGCTGCTCTAGGGATACTCAGGGGGCTCC
         TGCTCTCCTTCCCCTTCCCTTCTTGCCTCACCATTCCCCTAGGCAGGCCCTGCAGGTCCC
         ACACTCTCCCAGGCCCTAAACTTGGGCGGCCTTGCCCTGAGAGCTGGTCCTCCAGCGAGG

5583     AGGGAAAGGAGGAACAATTAGGACGTGGCAATGAGACCTGGCAGGGCAGAGTACAAGCCC
         AGCACCCAGTGTCCCAGCCTTAATGGGTCCTTACCATGGGCCAAACAGGGAGGGCTGATA
         CCTCCTTGCTCTTCCTAGATGCCCACCTCCTACAATCTCAGCCCACAAGTCCTCTCCACC
         TAGGGGGCTTGCTGCATGGCAATAACTCATAATTTGATTTGGAGGTTTGCCCTTTACAGG
         GGCAGATTTTCTGCTCAGTTCAACAATGAAATGAAGAGGAACTCCCTCTTTCTACAGCTC
         [C,T,A]
         CTTCTATCAGAGGCCCAGGTGCCTCAGAGCCACATTGAGTTGCTTTTTCTGGGATGAGGA
         AGTAGGGTTAAACTCCCCAGTTTCCTGAGGGAGGCTCCTGACAGGTGCCCTTTGTCAGAC
         CCTACCACAGCCTGGATAGGCAGCCACATTGGTCCTCGCCCTTGCTCGGCACTCCGTGGT
         GGTCCTGCCCTTCTCCCTGCATGCCTGTGGGTCTGCTCTGGTGTGTGAAGGTCGGTGGGT
         TAACTGTGTGCCTACTGAACCTGGCAAATAAACATCACCCTGCAAAGCCTCTGGCCACCC

6242     GGAGAGGCTGGGAGCAGGTTCACAAGTAGTGGCTGGGAGTAGTAGTGAACAGTGCCCTGT
         GGATTTCTTGGGCTGAGGGTGAAGATCATCCTCACCACAGTGTATTCCTCAATGGTGGTG
         GTGGTGGGGGTCCTCTGAACTCTAGAAATCCATGTGAGTAGTGGGTCTTGGGCTGCATTT
         GGACCAAGGAATACTCCCTGGGCTGAGAGCTCAAGTAAGGGCTGCTGTTTTTGACTCCTG
         TTGACCGAGGAGCCTTACTCTTGATTTAGGCATAGAGCTGGAATCTACCTGGGCCAGCCA
         [G,C]
         CGCAAGGACAGACCCTGCTCATAGCCAAAGATAGCTTCCCTGAGCTAGGGAGAGGGTGTA
         GGGTGAGCAATGCACAAAGATTCTATGCTGCTCTGTGTTGATTCCTTCTTTCTGTGAACA
         CCTGTGCTTTCCACCTATGCCCCAAATGAAATCTCACTCTGGGTCTATTTCAGCTGGAGC
         AGATCAGCTTTATATTATGGGACTATGCACAGGGTTTCTTCTGGGTAGAGGGAGTAACAC
         TGCCACAGATACTAAGCCTAAAAACCCAAAAGTTGACTTACTCCAGCCCAGGTGGGCCTG
```

FIGURE 3E

7264    CTATTCCCTTGCGGCTGCGGTTTTCTCTGCCTTGGCCCAGCCTGCCTCGCGCCAGCTCTG
        GCATGGGACCACAATGCGCTGCCTTGCCCTGGAAAAGGGTCCAGCTGGCAGCCTCGCTGC
        TCCCCGCCTTGATATAATGCTGCGCTCTCAAGTGGCAGGTCGAGTCTCCCCAGAGGACGC
        CTGAGAGCGACCGCGCTCCGCCCAGGATTCTCTACGGCCTCGGGGCCGCTAAGCCCCGCC
        CATAGTTCCGCCCATCCGAGAATTTGTCCAATCCAGGCGAAGTATTCACGCTCCGCCCAA
        [G,A]
        GTTTTGTGTTGTCACTTCCGGCCCGCTCCAGGAAGTCGTGCTGCGGAGCCAAATTTGAAG
        CAAGCGGAGGCGCGGGGGCGCGTCTACGAAGCCGGACCTGTAGCAGTTTCTTTGGCTGCC
        TGGGCCCCTTGAGTCCAGCCATCATGCCTATCCGTGCTCTGTGCACTATCTGCTCCGACT
        TCTTCGATCACTCCCGCGACGTGGCCGCCATCCACTGCGGCCACACCTTCCACTTGCAGT
        GGTGAGTGACTGCAGTGTTGGGGCCCGGTGTTTGCCCG

FIGURE 3F

SEQUENCE LISTING

<160> NUMBER OF SEQ ID NOS: 3

<210> SEQ ID NO 1
<211> LENGTH: 3124
<212> TYPE: DNA
<213> ORGANISM: HOMO SAPIEN

<400> SEQUENCE: 1

| | | | | | |
|---|---|---|---|---|---|
| tccgccccg | gcccggggtg | cgaatccggt | gccggcaagc | ggctggcgat | gctggaggtt | 60 |
| cgctagccga | agcggctgca | tctggcgccg | cgtctgcccc | gcgtgctcgg | agcggattct | 120 |
| gcccgccgtc | cccggagccc | tcggcgcccc | gctgagcccg | cgatcacttc | ctccctgtga | 180 |
| ccaaccggcg | ctgcaggtta | gagcctggca | atgccgtttg | ggtgtgtgac | tctgggcgac | 240 |
| aagaagaact | ataaccagcc | atcggaggtg | actgacagat | atgatttggg | acaggtcatc | 300 |
| aagactgagg | agttttgtga | aatcttccgg | gccaaggaca | agacgacagg | caagctgcac | 360 |
| acctgcaaga | agttccagaa | gcgggacggc | cgcaaggtgc | ggaaagctgc | caagaacgag | 420 |
| ataggcatcc | tcaagatggt | gaagcatccc | aacatcctac | agctggtgga | tgtgtttgtg | 480 |
| acccgcaagg | agtactttat | cttcctggag | ctggccacgg | ggagggaggt | gtttgactgg | 540 |
| atcctggacc | agggctacta | ctcggagcga | gacacaagca | acgtggtacg | gcaagtcctg | 600 |
| gaggccgtgg | cctatttgca | ctcactcaag | atcgtgcaca | ggaatctcaa | gctggagaac | 660 |
| ctggtttact | acaaccggct | gaagaactcg | aagattgtca | tcagtgactt | ccatctggct | 720 |
| aagctagaaa | atggcctcat | caaggagccc | tgtgggaccc | ccgagtatct | ggccccagag | 780 |

-continued

| | |
|---|---|
| gtggtaggcc ggcagcggta tggacgccct gtggactgct gggccattgg agtcatcatg | 840 |
| tacatcctgc tttcaggcaa tccaccttc tatgaggagg tggaagaaga tgattatgag | 900 |
| aaccatgata gaatctctt ccgcaagatc ctggctggtg actatgagtt tgactctcca | 960 |
| tattgggatg atatttcgca ggcagccaaa gacctggtca aaggctgat ggaggtggag | 1020 |
| caagaccagc ggatcactgc agaagaggcc atctcccatg agtggatttc tggcaatgct | 1080 |
| gcttctgata gaacatcaa ggatggtgtc tgtgcccaga ttgaaaagaa ctttgccagg | 1140 |
| gccaagtgga gaaggctgt ccgagtgacc accctcatga acggctccg ggcaccagag | 1200 |
| cagtccagca cggctgcagc ccagtcggcc tcagccacag acactgccac ccccggggct | 1260 |
| gcaggtgggg ccacagctgc agctgcgagt ggagctacct cagcccctga gggtgatgct | 1320 |
| gctcgtgctg caaagagtga taatgtggcc cccgcagacc gtagtgccac cccagccaca | 1380 |
| gatggaagtg ccaccccagc cactgatggc agtgtcaccc cagccaccga tggaagcatc | 1440 |
| actccagcca ctgatgggag tgtcacccca gtcactgaca ggagcgctac tccagccact | 1500 |
| gatgggagag ccacaccagc cacagaagag agcactgtgc ccaccaccca aagcagtgcc | 1560 |
| atgctggcca ccaaggcagc tgccacccct gagccggcta tggcccagcc ggacagcaca | 1620 |
| gccccagagg gcgccacagg ccaggctcca ccctctagta aggggaaga ggctgctggt | 1680 |
| tatgcccagg agtctcaaag ggaggaggcc agctgagtag gcagcctggt gagggggggc | 1740 |
| agggatggg caggagggtg ggagagtgga tgagggcttt ctcactgtac atagagtcac | 1800 |
| tggcatgatg ccctcgctcc cccatgcccc cacatcccag tggggcataa ctaggggtca | 1860 |
| cgggagagca gtctcgtctc ctgtgtgtat gtgtgtgagt ggtgggcagg ccagtggcag | 1920 |
| ggccggcccc agccctgca tggattcctt gtggcttttc tgtcttttgc tagcttcacc | 1980 |
| agtttctgtt ccttgtggga tgctgctcta gggatactca gggggctcct gctctccttc | 2040 |
| cccttcccctt cttgcctcac cattcccta ggcaggccct gcaggtccca cactctccca | 2100 |
| ggccctaaac ttgggcggcc ttgccctgag agctggtcct ccagcgaggc cctgtcagcg | 2160 |
| gtcttaggct cctgcacatg aaggtgtgtg cctgtggtgt gtgggctgct ctaggagcag | 2220 |
| atacaggctg gtatagagga tgcagaaagg tagggcagta tgtttaagtc cagacttggc | 2280 |
| acatggctag ggatactgct cactagctgt ggaggtcctc aggagtggag agaatgagta | 2340 |
| ggagggcaga agcttccatt tttgtccttc ctaagaccct gttatttgtg ttatttcctg | 2400 |
| cctttccgag tcctgcagtg ggctgccctg taccctgaac ctcatgagcc tctaagggaa | 2460 |
| aggaggaaca attaggacgt ggcaatgaga cctggcaggg cagagtacaa gcccagcacc | 2520 |
| cagtgtccca gccttactgg gtccttaccc tgggccaaac agggagggct gatacctcct | 2580 |
| tgctcttcct agatgcccac ctcctacaat ctcagcccac aagtcctctc caccctaggg | 2640 |
| ggcttgctgc atggcaataa ctcataatct gatttggagg tttgcccttt acaggggcag | 2700 |
| attttctgct cagttcaaca atgaaatgaa gaggaactcc ctctttctac agctcacttc | 2760 |
| tatcagaggc ccaggtgcct cagagccaca ttgagttgct tttctgggga tgaggaagta | 2820 |
| gggttaaact ccccagtttc ctgagggagg ctcctgacag gtgcccttg tcagaccta | 2880 |
| ccacagcctg gataggcagc cacattggtc ctcgcccttg ctcggcactc cgtggtggtc | 2940 |
| ctgcccttct ccctgcatgc ctgtgggtct gctctggtgt gtgaaggtcg gtgggttaac | 3000 |
| tgtgtgccta ctgaacctgg caaataaaca tcaccctgca agccaaaaa aaaaaaaaa | 3060 |
| aaaaaaaaaa aaaaaaaaa aaaaaaaaa aaaaaaaaa aaaaaaaaa aaaaaaaaa | 3120 |
| aaaa | 3124 |

<210> SEQ ID NO 2
<211> LENGTH: 501
<212> TYPE: PRT
<213> ORGANISM: HOMO SAPIEN

<400> SEQUENCE: 2

Met Pro Phe Gly Cys Val Thr Leu Gly Asp Lys Lys Asn Tyr Asn Gln
1               5                   10                  15

Pro Ser Glu Val Thr Asp Arg Tyr Asp Leu Gly Gln Val Ile Lys Thr
            20                  25                  30

Glu Glu Phe Cys Glu Ile Phe Arg Ala Lys Asp Lys Thr Thr Gly Lys
        35                  40                  45

Leu His Thr Cys Lys Lys Phe Gln Lys Arg Asp Gly Arg Lys Val Arg
    50                  55                  60

Lys Ala Ala Lys Asn Glu Ile Gly Ile Leu Lys Met Val Lys His Pro
65                  70                  75                  80

Asn Ile Leu Gln Leu Val Asp Val Phe Val Thr Arg Lys Glu Tyr Phe
                85                  90                  95

Ile Phe Leu Glu Leu Ala Thr Gly Arg Glu Val Phe Asp Trp Ile Leu
            100                 105                 110

Asp Gln Gly Tyr Tyr Ser Glu Arg Asp Thr Ser Asn Val Val Arg Gln
        115                 120                 125

Val Leu Glu Ala Val Ala Tyr Leu His Ser Leu Lys Ile Val His Arg
    130                 135                 140

Asn Leu Lys Leu Glu Asn Leu Val Tyr Tyr Asn Arg Leu Lys Asn Ser
145                 150                 155                 160

Lys Ile Val Ile Ser Asp Phe His Leu Ala Lys Leu Glu Asn Gly Leu
                165                 170                 175

Ile Lys Glu Pro Cys Gly Thr Pro Glu Tyr Leu Ala Pro Glu Val Val
            180                 185                 190

Gly Arg Gln Arg Tyr Gly Arg Pro Val Asp Cys Trp Ala Ile Gly Val
        195                 200                 205

Ile Met Tyr Ile Leu Leu Ser Gly Asn Pro Pro Phe Tyr Glu Glu Val
    210                 215                 220

Glu Glu Asp Asp Tyr Glu Asn His Asp Lys Asn Leu Phe Arg Lys Ile
225                 230                 235                 240

Leu Ala Gly Asp Tyr Glu Phe Asp Ser Pro Tyr Trp Asp Asp Ile Ser
                245                 250                 255

Gln Ala Ala Lys Asp Leu Val Thr Arg Leu Met Glu Val Glu Gln Asp
            260                 265                 270

Gln Arg Ile Thr Ala Glu Glu Ala Ile Ser His Glu Trp Ile Ser Gly
        275                 280                 285

Asn Ala Ala Ser Asp Lys Asn Ile Lys Asp Gly Val Cys Ala Gln Ile
    290                 295                 300

Glu Lys Asn Phe Ala Arg Ala Lys Trp Lys Lys Ala Val Arg Val Thr
305                 310                 315                 320

Thr Leu Met Lys Arg Leu Arg Ala Pro Glu Gln Ser Ser Thr Ala Ala
                325                 330                 335

Ala Gln Ser Ala Ser Ala Thr Asp Thr Ala Thr Pro Gly Ala Ala Gly
            340                 345                 350

Gly Ala Thr Ala Ala Ala Ala Ser Gly Ala Thr Ser Ala Pro Glu Gly
        355                 360                 365

Asp Ala Ala Arg Ala Ala Lys Ser Asp Asn Val Ala Pro Ala Asp Arg

```
                    370             375             380
Ser Ala Thr Pro Ala Thr Asp Gly Ser Ala Thr Pro Ala Thr Asp Gly
385             390             395             400

Ser Val Thr Pro Ala Thr Asp Gly Ser Ile Thr Pro Ala Thr Asp Gly
                405             410             415

Ser Val Thr Pro Val Thr Asp Arg Ser Ala Thr Pro Ala Thr Asp Gly
            420             425             430

Arg Ala Thr Pro Ala Thr Glu Glu Ser Thr Val Pro Thr Thr Gln Ser
        435             440             445

Ser Ala Met Leu Ala Thr Lys Ala Ala Thr Pro Glu Pro Ala Met
    450             455             460

Ala Gln Pro Asp Ser Thr Ala Pro Glu Gly Ala Thr Gly Gln Ala Pro
465             470             475             480

Pro Ser Ser Lys Gly Glu Glu Ala Ala Gly Tyr Ala Gln Glu Ser Gln
                485             490             495

Arg Glu Glu Ala Ser
            500

<210> SEQ ID NO 3
<211> LENGTH: 7542
<212> TYPE: DNA
<213> ORGANISM: HOMO SAPIEN

<400> SEQUENCE: 3
aatgaaatcc tgtatctaca aaaaatttt taaaaattag ccagttgtgg tggtgtgcac      60
ctatggtcca gtcctagcta ctcaggaggc tgaggtggga ggatcgcttg agcccaggag    120
gttgaggctg aatgagctg tgatcattcc actgcattcc agcctgggtg ccactgcatt    180
ccagcctggg tgacagaaca gctgggcatg gtgcgggtgc ctgtaatccc agctgcggtg    240
ggaggatcgt tgagttcag gagctctggg ctgcagtgcg ctatgccagt gggtgtcta    300 cactaagttt ggcattagta tggtgacttc ctgggagcta gagctcatca ggttgcctaa    360 aggagggtg aagcaaccaa ggtcagagac gaagcaggtc aaaactcctg tgctgatcag    420
tagtgggctt gtgcccatga atagccactg cactccagcc tgggcaacat agtgagactt    480
gtctctaaaa aagaaagaa agaaagaaaa gaaagaaaa gaaataggtc ttccagaatc    540 cccccccatgt gtcctgaatc aatcataacc cctccttttc tcttagaagg gaccattatc    600
tgactctgct tatttcctag ctttctttta tagctctact gctgtgtttg tatccccctt    660
acgggtttgt tctgcctgtt tgaactctat caatagactc atactatatg tattcttttg    720 tgtcttttg cacttaacac tgtgtaagag tcaccaggtg gttgggtata gctgtagctc    780
ctttgtttcc attgctatat aatattccat tgtgtgactc taccacaata catcctgttg    840
gtggtggtat ttggtctgtt ttcaatttttt ggcgattatg tatatggcta ctatgagcat    900
tgtatgactg tcctgatgca cgaatatgtg cacttctgta ggcacgtatt taggagtgca    960
attgctggtt catagggtat gtttgtttga ctttagtggt tttaccaaac tgctttacaa   1020 agggagttt gccctctcct agcagtgctc acgttcttca tatatccact aacacttgtt   1080
agctctagac cttcagagat gactagcagg tgggtgggtg gttatagccc ccttcatctg   1140
taaaatagct gaaatttaaa taaactgttt gataagcctt tttttgaatg tatagaatac   1200
aaaactattc cctatatat cagcttaata cattttttca tatgtaggct gttgcacttc   1260
aggcagccaa gctgagtagc tggatgtcta gccagaaaag caggggtagg atctaagcct   1320
gcctatcctc tagcccctcc tggtatggtc tctgccccta gcttggcctg agccaggttg   1380
```

```
gggtctccca aaagcagccc ctatgttgtg gggaagtgga gagtagtaca gctaagccag    1440 acccattgt gcccgcaggt tagagcctgg caatgccgtt tgggtgtgtg actctgggcg    1500
acaagaagaa ctataaccag ccatcggagg tgactgacag atatgatttg ggacaggtca    1560
tcaagacgtg agtgccgggc ctgtcaggca aggctgggtg ggctggtgag caggggctag    1620
ggaagtggca gtggagtgca gctgatgcta aggccaggcc tgagtgggtg cctgtcggct    1680
gcagtgagga gttttgtgaa atcttccggg ccaaggacaa gacgcaggc aagctgcaca    1740 cctgcaagaa gttccagaag cgggacgcc gcaaggtgcg gaaagctgcc aagaacgaga    1800
taggcatcct caagatgtga gtttgaggcc tgggattggg gcggggtggg aggcagcagg    1860
gaagggctta gagggcaagt ggcctcaggc agtcccagcc tctggccaat tagtactgct    1920
gtggccactg tggtgaccac agcctctccc agggttcat ccagccctaa ctactggctc    1980
ccctccctgt cgccagggtg aagcatccca acatcctaca gctggtggat gtgtttgtga    2040
cccgcaagga gtactttatc ttcctggagc tgtgagtgtg ggtctgggga cccaagattc    2100
cccagcgccc agggctttca cctgtcccac cctctgcagc taaggaaacc ccctttctgg    2160
acccttggcg tcccaggtcc ctgtgccttg ctcagccagc tgcctggcgt aggcagctca    2220
cccaagtgct cctgccctac ccctgattct gcccacgcca ggctcagggg ctggtgtccc    2280
tcagggccac ggggagggag gtgtttgact ggatcctgga ccagggctac tactcggagc    2340
gagacacaag caacgtggta cggcaagtcc tggaggccgt ggcctatttg cactcactca    2400
agatcgtgca caggaatctc aaggtgaggg cagagccaga gtcaaagggc cagttggcag    2460
ctgggctggt gctgggggtgg gcagcacctc agggccttgg tctagcctcc aaggtcctca    2520
tggtgtcttc tgctcaccca catgctattc tcacaccaca gctggagaac ctggtttact    2580
acaaccggct gaagaactcg aagattgtca tcagtgactt ccatctggct aagctagaaa    2640
atggcctcat caaggagccc tgtgggaccc ccgagtatct gggcaagcag ggggtggggc    2700
aggggcaggg ggataatggg gggcagcctt caggagctg ctctgggcag ggggaaaatg    2760
tgctcatctc aggaagctgg tgtggatggt actggacctg gctaggcctg atactgacca    2820
gcagatgggc gctgtgtttg tagccccaga ggtggtaggc cggcagcggt atggacgccc    2880
tgtggactgc tgggccattg gagtcatcat gtacatcctg tgagtggaca gatggacaag    2940
caggcttgca gtcagatggg gtgggggcat gtgtctgtgg cctttctgtg tgacccttcc    3000
cccatgcagg ctttcaggca acccacccttt ctatgaggag gtggaagaag atgattatga    3060
gaaccatgat aagaatctct tccgcaagat cctggctggt gactatgagt ttgactctcc    3120
atattgggat gatatttcgc aggcaggtga ggagtgcct gccagcact tggtagaacg    3180 caagggagtg gggagggtgt cctgctctca tcttcctctg tggtattctg cttctgtccc    3240
ccagcccatt tatcacctct agacattgag atggggtgcc catgactatc ccctccttgg    3300
ttttgtccac agccaaagac ctggtcacaa ggctgatgga ggtggagcaa gaccagcgga    3360
tcactgcaga agaggccatc tcccatgagt ggtgagcagg gtccagggga gggtgggaga    3420
ggccagggtc cccctcacac ccagcagccc catctttgag gcctagaagg ggtgcaggta    3480
cctagagctc agggcagccc agaggctctg cctggtagtc cctggatgcc acatagaagg    3540
gctgagcaga gtctccacaa aggctcattc tctcagatcc agacacactt gcacccttt    3600 caggatttct ggcaatgctg cttctgataa gaacatcaag gatggtgtct gtgcccagat    3660
tgaaaagaac tttgccaggg ccaagtggaa ggtaaggctt ggataactcc cttccttggct    3720
```

-continued

```
ctatcccaag tattgcttct ggcactcagt ttcttgcctg catcacaccc ctgcagccac      3780
acacaagctt ttctcaggcc atcaggtgtg ggtgtagcca ctgtgattac cttaagtagg      3840
agtgctgagc agctgagtac ttggccctgg ggtggatgga ggtggccggg ggtactatgg      3900
aaggagtttg gtttggtcac tgccaagcaa tggatccagc aagcctcacc cttagccttt      3960
ctccactgtg ctcctttcag aaggctgtcc gagtgaccac cctcatgaaa cggctccggg      4020
caccagagca gtccagcacg gctgcagccc agtcggcctc agccacagac actgccaccc      4080
ccggggctgc aggtggggcc acagctgcag ctgcgagtgg agctacctca gcccctgagg      4140
gtgatgctgc tcgtgctgca aagagtgata atgtggcccc cgcagaccgt agtgccaccc      4200
cagccacaga tggaagtgcc acccagcca ctgatggcag tgtcacccca gccaccgatg       4260
gaagcatcac tccagccact gatgggagtg tcaccccagc cactgacagg agcgctactc      4320
cagccactga tgggagagcc acaccagcca cagaagagag cactgtgccc accacccaaa      4380
gcagtgccat gctgccacc aaggcagctg ccaccctga gccggctatg gcccagccgg        4440
acagcacagc cccagagggc gccacaggcc aggctccacc ctctagtaaa ggggaagagg      4500
ctgctggtta tgcccaggag tctcaaaggg aggaggccag ctgagtaggc agcctggtga      4560
gggggggcag gggatgggca ggaggtggg agagtggatg aggggcttct cactgtacat       4620
agagtcactg gcatgatgcc ctcgctcccc catgccccca catcccagtg gggcataact      4680
aggggtcacg ggagagcagt ctcgtctcct gtgtgtatgt gtgtgagtgg tgggcaggcc      4740
agtggcaggg ccggccccag cccctgcatg gattccttgt ggcttttctg tcttttgcta      4800
gcttcaccag tttctgttcc ttgtgggatg ctgctctagg gatactcagg gggctcctgc      4860
tctccttccc cttcccttct tgcctcacca ttcccctagg caggccctgc aggtcccaca      4920
ctctcccagg ccctaaactt gggcggcctt gccctgagag ctggtcctcc agcgaggccc      4980
tgtcagcggt cttaggctcc tgcacatgaa ggtgtgtgcc tgtggtgtgt gggctgctct      5040
aggagcagat acaggctggt atagaggatg cagaaaggta gggcagtatg tttaagtcca      5100
gacttggcac atggctaggg atactgctca ctagctgtgg aggtcctcag gagtggagag      5160
aatgagtagg agggcagaag cttccatttt tgtccttcct aagaccctgt tatttgtgtt      5220
atttcctgcc tttccgagtc ctgcagtggg ctgccctgta ccctgaacct catgagcctc      5280
taagggaaag gaggaacaat taggacgtgg caatgagacc tggcagggca gagtacaagc      5340
ccagcaccca gtgtcccagc cttaatgggt ccttaccatg ggccaaacag ggagggctga      5400
tacctccttg ctcttcctag atgcccacct cctacaatct cagcccacaa gtcctctcca      5460 cctaggggc ttgctgcatg gcaataactc ataatttgat ttggaggttt gcccttaca       5520 ggggcagatt ttctgctcag ttcaacaatg aaatgaagag gaactccctc tttctacagc      5580
tcacttctat cagaggccca ggtgcctcag agccacattg agttgctttt ctgggatga      5640 ggaagtaggg ttaaactccc cagtttcctg agggaggctc ctgacaggtg ccctttgtca      5700
gaccctacca cagcctggat aggcagccac attggtcctc gcccttgctc ggcactccgt      5760
ggtggtcctg cccttctccc tgcatgcctg tgggtctgct ctggtgtgtg aaggtcggtg      5820
ggttaactgt gtgcctactg aacctggcaa ataaacatca ccctgcaaag cctctggcca      5880
ccctctcgcc tttgcttcct ctgtcctact ggggaggagc cctggaagg cagtggggaa       5940 gggagaggct gggagcaggt tcacaagtag tggctgggag tagtagtgaa cagtgccctg      6000
tggatttctt gggctgaggg tgaagatcat cctcaccaca gtgtattcct caatggtggt      6060
ggtggtgggg gtcctctgaa ctctagaaat ccatgtgagt agtgggtctt gggctgcatt      6120
```

```
tggaccaagg aatactccct gggctgagag ctcaagtaag ggctgctgtt tttgactcct    6180
gttgaccgag gagccttact cttgatttag gcatagagct ggaatctacc tgggccagcc    6240
agcgcaagga cagaccctgc tcatagccaa agatagcttc cctgagctag ggagagggtg    6300
tagggtgagc aatgcacaaa gattctatgc tgctctgtgt tgattccttc tttctgtgaa    6360
cacctgtgct ttccacctat gccccaaatg aaatctcact ctgggtctat ttcagctgga    6420
gcagatcagc tttatattat gggactatgc acagggtttc ttctgggtag agggagtaac    6480
actgccacag atactaagcc taaaaaccca aaagttgact tactccagcc caggtgggcc    6540
tgggtgaact caccagggat gctgctctct gggaggacct caaagataac ctcctcaagg    6600
ataacttctc tgatgtggga ataataaaaa ggatttgtta gtctctagtc tttgaagcat    6660
ctgggcctcc aaaattccaa ccctactaca gtctcaagca taactgatcc tcctgagagc    6720
taagagctaa agtcagggta ctgccctag tgtctccaaa ctcaaggata gtcatatctt    6780
acttggatga agccaaggtt ggcctggggt gacctgaggg actggggcct atgtgtccat    6840
ctttctagaa tcgcccggaa ctgaggactg agagggtagg gtattgtggt ctatgggaac    6900
tacagaccat agcgcatggt ccatcactgt ccagagccca agggacccat cgggaccatt    6960
gttctattcc cttgcggctg cggttttctc tgccttggcc cagcctgcct cgcgccagct    7020
ctggcatggg accacaatgc gctgccttgc cctggaaaag ggtccagctg gcagcctcgc    7080
tgctccccgc cttgatataa tgctgcgctc tcaagtggca ggtcgagtct ccccagagga    7140
cgcctgagag cgaccgcgct ccgcccagga ttctctacgg cctcggggcc gctaagcccc    7200
gcccatagtt ccgcccatcc gagaatttgt ccaatccagg cgaagtattc acgctccgcc    7260
caaagttttg tgttgtcact tccggcccgc tccaggaagt cgtgctgcgg agccaaattt    7320
gaagcaagcg gaggcgcggg ggcgcgtcta cgaagccgga cctgtagcag tttctttggc    7380
tgcctgggcc ccttgagtcc agccatcatg cctatccgtg ctctgtgcac tatctgctcc    7440
gacttcttcg atcactcccg cgacgtggcc gccatccact gcggccacac cttccacttg    7500
cagtggtgag tgactgcagt gttggggccc ggtgtttgcc cg                      7542
```

ISOLATED HUMAN KINASE PROTEINS

RELATED APPLICATIONS

The present application is a divisional of U.S. application Ser. No. 09/734,030, filed on Dec. 12, 2000 and issued on Oct. 8, 2002, as U.S. Pat. No. 6,461,846, which claims benefit of U.S. Provisional Applicaion No. 60/207,281, filed on May 30, 2000.

FIELD OF THE INVENTION

The present invention is in the field of kinase proteins that are related to the calmodulin-binding kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Calmodulin-Binding Kinases

Calmodulin-binding protein kinases, including calcium/calmodulin (CaM) dependent protein kinases, are members of the STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Calmodulin is a major Ca(2+)-binding protein in the brain, where it modulates numerous Ca(2+)-dependent enzymes and cellular functions. Ca2+/calmodulin-dependent protein kinase II (CaMKII) is particularly important in the brain and is involved in a variety of neuronal functions (Sola et al., *Prog Neurobiol* June 1999;58(3):207–32), such as postsynaptic responses (such as long-term potentiation), neurotransmitter synthesis and exocytosis, cytoskeletal interactions and gene transcription (Colbran, *Neurochem Int* December 1992;21(4):469–97). Ca2+ and calmodulin antagonists inhibit seizures induced by convulsant agents, indicating that the Ca2+/calmodulin signaling system plays an important role in the onset of seizures. Changes in CaMKII expression has been observed following seizures and, furthermore, expression of calmodulin and CaMKII in microglial cells in the brain increases following seizures (Sola et al., *Prog Neurobiol* June 1999;58(3):207–32). CaMKII levels are also altered in pathological states such as Alzheimer's disease and ischemia (Colbran, *Neurochem Int* December 1992;21(4):469–97), suggesting a role of CaMKII in these disorders.

Calmodulin is also important for regulating the plasma membrane calcium pump, which transports Ca2+ out of cells. The pump is inactive in the absence of calmodulin, but is activated by calmodulin binding (Penniston et al., *J Membr Biol* Sep. 15 1998;165(2):101–9).

Kinase proteins, particularly members of the calmodulin-binding kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the calmodulin-binding kinase subfamily.

SUMMARY OF THE INVENTION

The present invention is based in part on the identification of amino acid sequences of human kinase peptides and proteins that are related to the calmodulin-binding kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in the brain (including infant and adult brain), lung, and hippocampus.

DESCRIPTION OF THE FIGURE SHEETS

FIGS. 1A–1B provide the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the brain (including infant and adult brain), lung, and hippocampus.

FIGS. 2A–2D provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3B provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at nine different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the calmodulin-binding kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the calmodulin-binding kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the calmodulin-binding kinase subfamily and the expression pattern observed. Experimental data as provided in FIG. 1 indicates expression in humans in the brain (including infant and adult brain), lung, and hippocampus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known calmodulin-binding family or subfamily of kinase proteins.

Specific Embodiments

Peptide Molecules

The present invention provides nucleic acid sequences that encode protein molecules that have been identified as being members of the kinase family of proteins and are related to the calmodulin-binding kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in the brain (including infant and adult brain), lung, and hippocampus. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the gene encoding the novel human kinase provided by the present invention is located on public BAC AC068701, which is known to be mapped to chromosome 3.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the gene encoding the novel human kinase provided by the present invention is located on public BAC AC068701, which is known to be mapped to chromosome 3. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at nine different nucleotide positions, including six positions outside the ORF. SNPs outside the ORF may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in humans in the brain (including infant and adult brain), lung, and hippocampus. Specifically, a virtual northern blot shows expression in the brain (adult and infant) and lung. In addition, PCR-based tissue screening panels indicate expression in the infant brain and hippocampus. A large percentage of pharmaceutical agents are being developed that modulate the activity of kinase proteins, particularly members of the calmodulin-binding subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the brain (including infant and adult brain), lung, and hippocampus. Such uses can readily be determined using the information provided herein, that which is known in the art, and routine experimentation.

The proteins of the present invention (including variants and fragments that may have been disclosed prior to the present invention) are useful for biological assays related to kinases that are related to members of the calmodulin-binding subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in humans in the brain (including infant and adult brain), lung, and hippocampus. Specifically, a virtual northern blot shows expression in the brain (adult and infant) and lung. In addition, PCR-based tissue screening panels indicate expression in the infant brain and hippocampus.

The proteins of the present invention are also useful in drug screening assays, in cell-based or cell-free systems. Cell-based systems can be native, i.e., cells that normally express the kinase, as a biopsy or expanded in cell culture.

Experimental data as provided in FIG. 1 indicates expression in humans in the brain (including infant and adult brain), lung, and hippocampus. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in humans in the brain (including infant and adult brain), lung, and hippocampus. Specifically, a virtual northern blot shows expression in the brain (adult and infant) and lung. In addition, PCR-based tissue screening panels indicate expression in the infant brain and hippocampus.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in the brain (including infant and adult brain), lung, and hippocampus. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the brain (including infant and adult brain), lung, and hippocampus. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the brain (including infant and adult brain), lung, and hippocampus. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in humans in the brain (including infant and adult brain), lung, and hippocampus. Specifically, a virtual northern blot shows expression in the brain (adult and infant) and lung. In addition, PCR-based tissue screening panels indicate expression in the infant brain and hippocampus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the brain (including infant and adult brain), lung, and hippocampus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the brain (including infant and adult brain), lung, and hippocampus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the brain (including infant and adult brain), lung, and hippocampus. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the gene encoding the novel human kinase provided by the present invention is located on public BAC AC068701, which is known to be mapped to chromosome 3.

FIG. 3 provides information on SNPs that have been found in the gene encoding the kinase protein of the present invention. SNPs were identified at nine different nucleotide positions, including six positions outside the ORF. SNPs outside the ORF may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at nine different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the gene encoding the novel human kinase provided by the present invention is located on public BAC AC068701, which is known to be mapped to chromosome 3.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in humans in the brain (including infant and adult brain), lung, and hippocampus. Specifically, a virtual northern blot shows expression in the brain (adult and infant) and lung. In addition, PCR-based tissue screening panels indicate expression in the infant brain and hippocampus. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in humans in the brain (including infant and adult brain), lung, and hippocampus. Specifically, a virtual northern blot shows expression in the brain (adult and infant) and lung. In addition, PCR-based tissue screening panels indicate expression in the infant brain and hippocampus.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in the brain (including infant and adult brain), lung, and hippocampus. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or downregulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in humans in the brain (including infant and adult brain), lung, and hippocampus. Specifically, a virtual northern blot shows expression in the brain (adult and infant) and lung. In addition, PCR-based tissue screening panels indicate expression in the infant brain and hippocampus. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in the brain (including infant and adult brain), lung, and hippocampus.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at nine different nucleotide positions, including six positions outside the ORF. SNPs outside the ORF may affect control/regulatory elements. As indicated by the data presented in FIG. 3, the gene encoding the novel human kinase provided by the present invention is located on public BAC AC068701, which is known to be mapped to chromosome 3. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at nine different nucleotide positions, including six positions outside the ORF. SNPs outside the ORF may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in humans in the brain (including infant and adult brain), lung, and hippocampus. Specifically, a virtual northern blot shows expression in the brain (adult and infant) and lung. In addition, PCR-based tissue screening panels indicate expression in the infant brain and hippocampus. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at nine different nucleotide positions, including six positions outside the ORF. SNPs outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated polypeptide having an amino acid sequence comprising SEQ ID NO:2.

3. A composition comprising the polypeptide of claim 1 and a carrier.

4. A composition comprising the polypeptide of claim 2 and a carrier.

* * * * *